(12) United States Patent
Demmer et al.

(10) Patent No.: US 12,138,461 B2
(45) Date of Patent: Nov. 12, 2024

(54) INPUT SWITCHING IN A VENTRICULAR INTRACARDIAC PACEMAKER

(71) Applicant: Medtronic, Inc., Minneapolis, MN (US)

(72) Inventors: Wade M. Demmer, Coon Rapids, MN (US); Yong K. Cho, Excelsior, MN (US); Mark K. Erickson, Brooklyn Park, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 590 days.

(21) Appl. No.: 17/391,118

(22) Filed: Aug. 2, 2021

(65) Prior Publication Data

US 2021/0353946 A1 Nov. 18, 2021

Related U.S. Application Data

(63) Continuation of application No. 16/449,517, filed on Jun. 24, 2019, now Pat. No. 11,077,307, which is a (Continued)

(51) Int. Cl.
*A61N 1/368* (2006.01)
*A61N 1/365* (2006.01)
(Continued)

(52) U.S. Cl.
CPC ....... *A61N 1/3688* (2013.01); *A61N 1/36514* (2013.01); *A61N 1/36585* (2013.01);
(Continued)

(58) Field of Classification Search
CPC .......................... A61N 1/3688; A61N 1/36514
(Continued)

(56) References Cited

U.S. PATENT DOCUMENTS 4,485,813 A 12/1984 Anderson et al.
4,559,947 A 12/1985 Renger et al.
(Continued)

FOREIGN PATENT DOCUMENTS

CN 104363956 A 2/2015
CN 104797292 A 7/2015
(Continued)

OTHER PUBLICATIONS

Chinese Communication dated Sep. 19, 2022, corresponding to counterpart Chinese Patent Application No. 201780076871.3; 11 pages.
(Continued)

*Primary Examiner* — Nadia A Mahmood

(57) ABSTRACT

An intracardiac pacemaker system is configured to produce physiological atrial event signals by a sensing circuit of a ventricular intracardiac pacemaker and select a first atrial event input as the physiological atrial event signals. The ventricular intracardiac pacemaker detects atrial events from the selected first atrial event input, determines if input switching criteria are met, and switches from the first atrial event input to a second atrial event input in response to the input switching criteria being met. The second atrial event input includes broadcast atrial event signals produced by a second implantable medical device and received by the ventricular intracardiac pacemaker.

21 Claims, 8 Drawing Sheets

Related U.S. Application Data continuation of application No. 15/377,717, filed on Dec. 13, 2016, now Pat. No. 10,328,270.

(51) Int. Cl.
*A61N 1/37* (2006.01)
*A61N 1/372* (2006.01)
*A61N 1/375* (2006.01)
*A61N 1/362* (2006.01)

(52) U.S. Cl.
CPC ......... *A61N 1/3682* (2013.01); *A61N 1/3704* (2013.01); *A61N 1/37288* (2013.01); *A61N 1/3756* (2013.01); *A61N 1/3627* (2013.01)

(58) Field of Classification Search
USPC .......................................................... 607/18
See application file for complete search history.

(56) References Cited

U.S. PATENT DOCUMENTS

| | | |
|---|---|---|
| 4,846,195 A | 7/1989 | Alt |
| 5,052,388 A | 10/1991 | Sivula et al. |
| 5,065,759 A | 11/1991 | Begemann et al. |
| 5,144,949 A | 9/1992 | Olson |
| 5,480,412 A | 1/1996 | Mouchawar et al. |
| 5,496,361 A | 3/1996 | Moberg et al. |
| 5,507,782 A | 4/1996 | Kieval et al. |
| 5,593,431 A | 1/1997 | Sheldon |
| 5,683,432 A | 11/1997 | Goedeke et al. |
| 5,720,769 A | 2/1998 | van Oort et al. |
| 5,836,987 A | 11/1998 | Baumann et al. |
| 5,861,011 A | 1/1999 | Stoop |
| 5,885,471 A | 3/1999 | Ruben et al. |
| 6,044,297 A | 3/2000 | Sheldon et al. |
| 6,295,471 B1 | 9/2001 | Bornzin et al. |
| 6,650,940 B1 | 11/2003 | Zhu et al. |
| 6,738,669 B1 | 5/2004 | Sloman et al. |
| 7,031,772 B2 | 4/2006 | Condie et al. |
| 7,062,328 B1 | 6/2006 | Levine et al. |
| 7,127,289 B2 | 10/2006 | Yu et al. |
| 7,130,681 B2 | 10/2006 | Gebhardt et al. |
| 7,200,437 B1 | 4/2007 | Nabutovsky et al. |
| 7,565,195 B1 | 7/2009 | Kroll et al. |
| 7,630,767 B1 | 12/2009 | Poore et al. |
| 7,634,313 B1 | 12/2009 | Kroll et al. |
| 7,904,155 B2 | 3/2011 | Yu et al. |
| 8,103,344 B2 | 1/2012 | Björling |
| 8,214,036 B2 | 7/2012 | Casset |
| 8,233,981 B2 | 7/2012 | Casset |
| 8,433,409 B2 | 4/2013 | Johnson et al. |
| 8,532,785 B1 | 9/2013 | Crutchfield et al. |
| 8,541,131 B2 | 9/2013 | Lund et al. |
| 8,792,980 B2 | 7/2014 | Yu et al. |
| 8,798,745 B2 | 8/2014 | Jacobson |
| 8,923,963 B2 | 12/2014 | Bonner et al. |
| 8,996,109 B2 | 3/2015 | Karst et al. |
| 9,272,146 B2 | 3/2016 | Anselmi |
| 9,278,218 B2 | 3/2016 | Karst et al. |
| 9,399,140 B2 | 7/2016 | Cho et al. |
| 9,427,594 B1 | 8/2016 | Bornzin et al. |
| 9,937,352 B2 | 4/2018 | Sheldon et al. |
| 10,080,900 B2 | 9/2018 | Ghosh et al. |
| 10,143,424 B2 | 12/2018 | Gunderson et al. |
| 10,286,214 B2 | 5/2019 | Demmer et al. |
| 2006/0265016 A1 | 11/2006 | Kim et al. |
| 2012/0095521 A1 | 4/2012 | Hintz |
| 2012/0172892 A1 | 7/2012 | Grubac et al. |
| 2012/0221068 A1 | 8/2012 | Ellingson |
| 2013/0138006 A1 | 5/2013 | Bornzin et al. |
| 2013/0325081 A1 | 12/2013 | Karst et al. |
| 2014/0121721 A1 | 5/2014 | Ghanem et al. |
| 2015/0217119 A1 | 8/2015 | Nikolski et al. |
| 2015/0224315 A1 | 8/2015 | Stahmann |
| 2015/0335894 A1* | 11/2015 | Bornzin ............... A61N 1/3756 607/18 |
| 2016/0011416 A1 | 1/2016 | Kobayashi |
| 2016/0015287 A1 | 1/2016 | Anderson et al. |
| 2016/0015984 A1 | 1/2016 | Demmer et al. |
| 2016/0015985 A1 | 1/2016 | Cho et al. |
| 2016/0023000 A1 | 1/2016 | Cho et al. |
| 2016/0067486 A1 | 3/2016 | Brown et al. |
| 2016/0067487 A1 | 3/2016 | Demmer et al. |
| 2016/0067490 A1 | 3/2016 | Carney et al. |
| 2016/0067500 A1 | 3/2016 | Demmer et al. |
| 2016/0114162 A1 | 4/2016 | Sheldon et al. |
| 2016/0114168 A1 | 4/2016 | Demmer et al. |
| 2016/0114169 A1 | 4/2016 | Sheldon et al. |
| 2016/0129263 A1 | 5/2016 | Demmer et al. |
| 2016/0144190 A1 | 5/2016 | Cao et al. |
| 2016/0167487 A1 | 6/2016 | Tamarapoo et al. |
| 2016/0250478 A1 | 9/2016 | Greenhut et al. |
| 2016/0310733 A1 | 10/2016 | Sheldon et al. |
| 2017/0028194 A1 | 2/2017 | Bonner et al. |
| 2017/0028206 A1 | 2/2017 | Ghosh |
| 2018/0085588 A1 | 3/2018 | Splett et al. |
| 2018/0085589 A1 | 3/2018 | Splett et al. |
| 2019/0111271 A1 | 4/2019 | Demmer et al. |

FOREIGN PATENT DOCUMENTS

| | | |
|---|---|---|
| WO | 2016064663 A1 | 4/2016 |
| WO | 2016094175 A1 | 6/2016 |
| WO | 2016144575 A1 | 9/2016 |

OTHER PUBLICATIONS (PCT/US2017/066001) PCT Notification of Transmittal of the International Search Report and the Written Opinion of the International Searching Authority, Mailed Apr. 24, 2018, 14 pages.

* cited by examiner

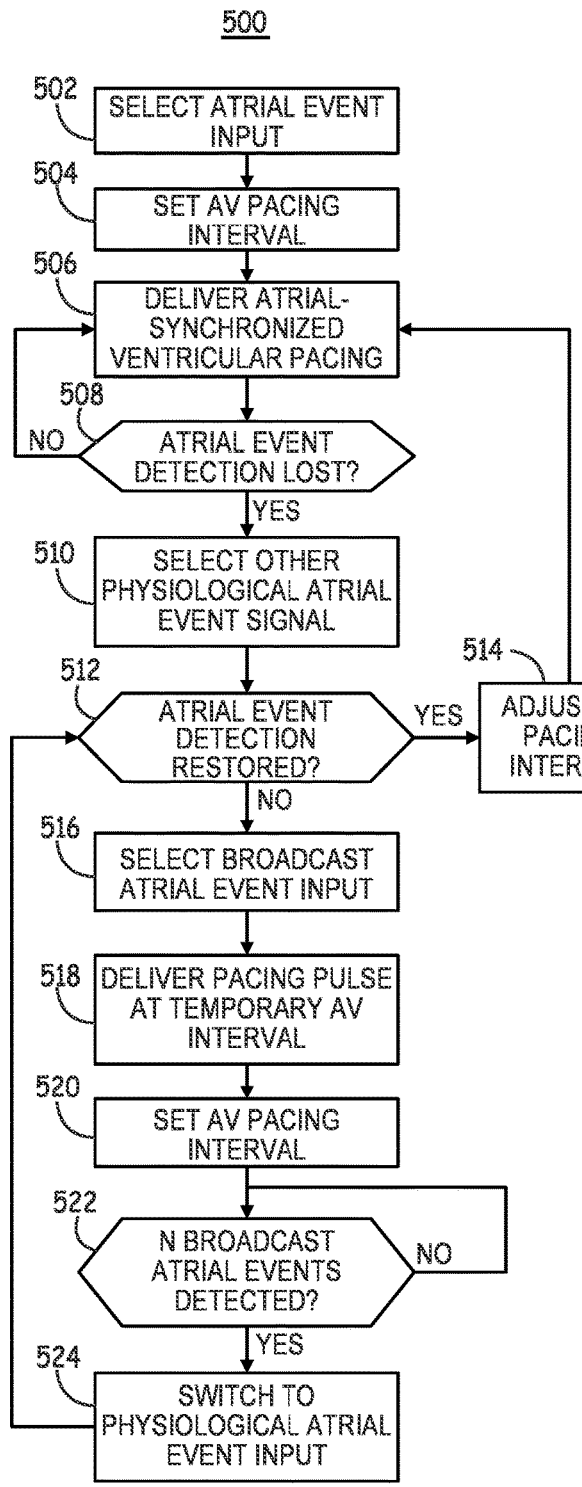
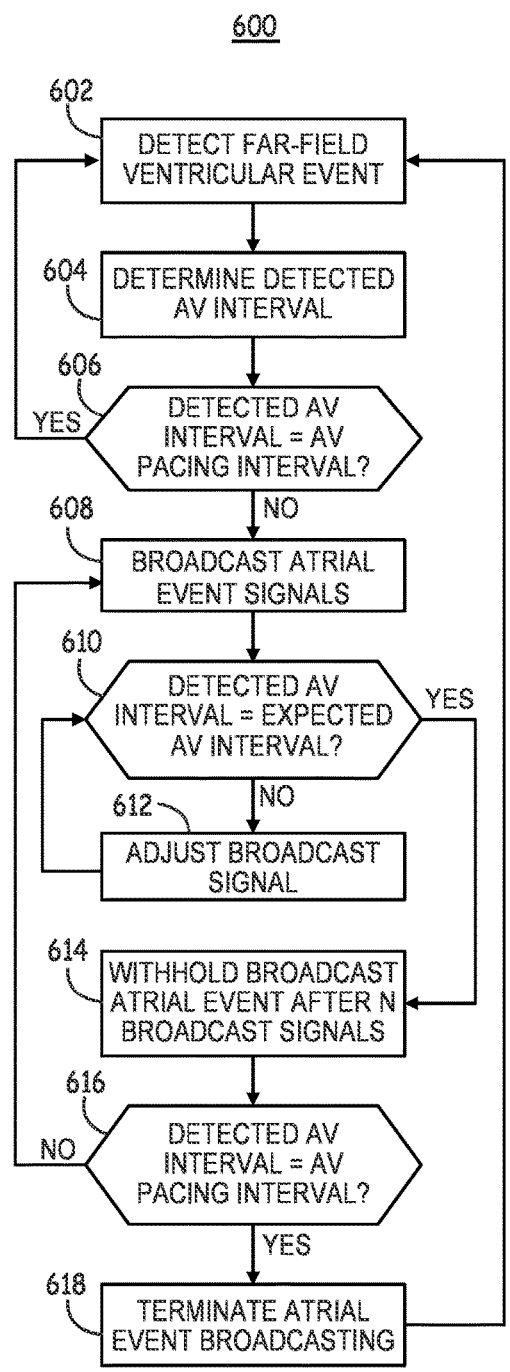
FIG. 9
FIG. 10

INPUT SWITCHING IN A VENTRICULAR INTRACARDIAC PACEMAKER

REFERENCE TO RELATED APPLICATIONS

This application is a Continuation of U.S. patent application Ser. No. 16/449,517 filed on Jun. 24, 2019, which is a Continuation of U.S. patent application Ser. No. 15/377,717, filed on Dec. 13, 2016, now U.S. Pat. No. 10,328,270, the content of all of which is incorporated herein by reference in its entirety.

TECHNICAL FIELD

The disclosure relates to an intracardiac pacing system including a ventricular pacemaker and an associated method for switching between atrial event inputs used for detecting atrial events and controlling atrial-synchronized ventricular pacing pulses by the ventricular pacemaker.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, other conditions may require atrial and ventricular (dual chamber) sensing for providing atrial-synchronized ventricular pacing in order to maintain a regular heart rhythm.

SUMMARY

In general, the disclosure is directed to a intracardiac pacemaker system and techniques for selecting an atrial event input used by a ventricular intracardiac pacemaker for detecting atrial events and controlling atrial-synchronized ventricular pacing. A system operating according to the techniques disclosed herein switches from a first atrial event input to a second atrial event input in response to input switching criteria being met. The first atrial event input may be physiological atrial event signals produced by a sensing circuit of the ventricular intracardiac pacemaker. The second atrial event input may be broadcast atrial event signals produced by a second implantable medical device, which may be an atrial intracardiac pacemaker. Input switching criteria may include a loss of detected atrial events for one or more ventricular cycles, a threshold patient heart rate, a patient posture known to be associated with unreliable atrial event detection, a threshold level of patient physical activity or any combination thereof.

In one example, the disclosure provides an intracardiac pacemaker system including a ventricular intracardiac pacemaker having a pulse generator, a sensing circuit, a receiving circuit, and a control circuit coupled to the pulse generator, the sensing circuit, and the receiving circuit. The pulse generator is configured to generate and deliver pacing pulses to a ventricle of a patient's heart via electrodes coupled to the ventricular intracardiac pacemaker. The sensing circuit is configured to produce physiological atrial event signals. The receiving circuit is configured to receive broadcast atrial event signals that are broadcast by a second implantable medical device. The control circuit is configured to select a first atrial event input as the physiological atrial event signals, detect first atrial events from the selected first atrial event input, determine if input switching criteria are met, switch from the first atrial event input to a second atrial event input in response to the input switching criteria being met, the second atrial event input being the broadcast atrial event signals. The control circuit is configured to detect second atrial events from the second atrial event input and set an atrioventricular (AV) pacing interval in response to detecting each of the first atrial events and the second atrial events for controlling the pulse generator to deliver the ventricular pacing pulses.

In another example, the disclosure provides a method performed by an intracardiac pacemaker system. The method includes producing physiological atrial event signals by a sensing circuit of a ventricular intracardiac pacemaker and selecting a first atrial event input by a control circuit of the ventricular intracardiac pacemaker as the physiological atrial event signals. The method further includes detecting first atrial events from the selected first atrial event input, determining if input switching criteria are met and switching from the first atrial event input to a second atrial event input in response to the input switching criteria being met. The second atrial event input includes broadcast atrial event signals that are broadcast by a second implantable medical device and received by a receiving circuit of the ventricular intracardiac pacemaker. The method further includes detecting second atrial events from the second atrial event input and setting an AV pacing interval in response to detecting each of the first atrial events and the second atrial events for controlling a pulse generator of the ventricular intracardiac pacemaker to deliver pacing pulses to a ventricle of a patient's heart via electrodes coupled to the ventricular intracardiac pacemaker.

In another example, the disclosure provides a non-transitory, computer-readable medium storing a set of instructions, which, when executed by control circuitry of an implantable medical device system including a ventricular intracardiac pacemaker and a second implantable medical device, cause the system to produce physiological atrial event signals by a sensing circuit of the ventricular intracardiac pacemaker, select a first atrial event input received as the physiological atrial event signals, detect first atrial events from the selected first atrial event input, determine if input switching criteria are met and switch from the first atrial event input to a second atrial event input in response to the input switching criteria being met. The second atrial event input includes broadcast atrial event signals that are broadcast by the second implantable medical device and received by the ventricular intracardiac pacemaker. The system is further caused to detect second atrial events from the second atrial event input and set an AV pacing interval in response to detecting each of the first atrial events and the second atrial events for controlling a pulse generator of the ventricular intracardiac pacemaker to deliver pacing pulses to a ventricle of a patient's heart via electrodes coupled to the ventricular intracardiac pacemaker.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

FIG. 9 is a flow chart of a method performed by the RV pacemaker of FIG. 1 for controlling atrial event input during atrial-synchronized ventricular pacing according to one example.

FIG. 10 is a flow chart of a method performed by the RA pacemaker of FIG. 1 for controlling broadcasting of atrial event signals to the RV pacemaker.

DETAILED DESCRIPTION

Figure 1:
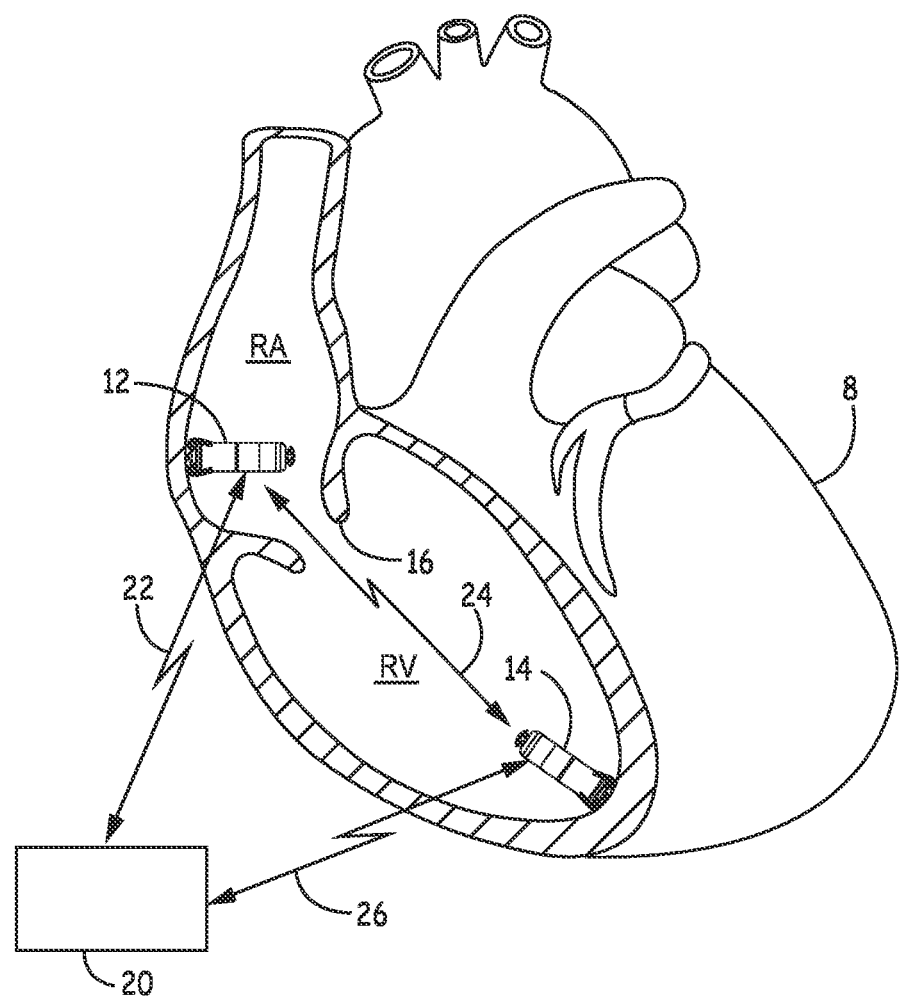
FIG. 1 is a conceptual diagram illustrating an intracardiac pacing system that may be used to sense cardiac signals and deliver atrial-synchronized ventricular pacing pulses.

During atrial-synchronized ventricular pacing, ventricular pacing pulses are delivered at an AV pacing interval following an atrial event to provide proper hemodynamic synchrony between the atrial contraction and the ventricular contraction. In order for a ventricular intracardiac pacemaker to provide atrial-synchronized ventricular pacing, the ventricular intracardiac pacemaker needs to sense or detect an atrial event on each cardiac cycle to start the AV pacing interval. As the atrial rate increases or decreases during normal physiological heart rate changes, the ventricular pacing rate tracks the atrial rate. This atrial-synchronized ventricular pacing is referred to as an "atrial-tracking" pacing mode. In a non-atrial tracking ventricular pacing mode, or when an atrial event is not detected for starting the AV pacing interval, the ventricular pacing pulses are delivered at a ventricular lower rate (LR) pacing interval that is independent of atrial events and does not track the atrial rate but does prevent ventricular asystole in a patient with AV block. Generally, atrial-synchronized ventricular pacing mode is desirable over a non-atrial tracking pacing when the sinus node of the heart is functioning normally in setting the intrinsic atrial rate or the atria are being paced at an appropriate pacing rate for the patient's level of physical activity.

In order to provide optimal synchrony between atrial systolic events and ventricular systole, a ventricular intracardiac pacemaker needs to receive reliable atrial event input signals indicative of the timing of the atrial systolic event. Atrial event input signals may be atrial P-wave signals included in the cardiac electrical signal received by the ventricular intracardiac pacemaker, atrial mechanical event signals included in a motion sensor signal such as an accelerometer signal, far-field atrial pacing pulse signals included in the cardiac electrical signal received by the ventricular intracardiac pacemaker, or wireless communication signals transmitted from an atrial intracardiac pacemaker to the ventricular intracardiac pacemaker. The detection of these various atrial event input signals may have different power requirements and differing reliability over time, between patients, and compared to each other.

For example, receiving a wireless communication signal on a beat-by-beat basis may require considerable more power than sensing a P-wave from the cardiac electrical signal received by the ventricular intracardiac pacemaker. P-wave sensing by a ventricular intracardiac pacemaker, however, may be challenging due to the relatively small far-field P-wave signal amplitude compared to the near-field R-wave signal amplitude. Atrial systolic mechanical events detected from a motion sensor signal may be reliable when the patient is at rest, but, during periods of increased patient physical activity or exercise, detection of atrial mechanical event signals may be confounded by patient physical activity signals included in the motion sensor signal. Techniques are disclosed herein for selecting an atrial event input and switching between atrial event inputs for providing efficient and reliable atrial event detection and atrial tracking by ventricular pacing pulses delivered by a ventricular intracardiac pacemaker.

FIG. 1 is a conceptual diagram illustrating an intracardiac pacing system 10 that may be used to sense cardiac signals and deliver atrial-synchronized ventricular pacing pulses. IMD system 10 includes a right ventricular (RV) intracardiac pacemaker 14 and a right atrial (RA) intracardiac pacemaker 12 in some examples. Pacemakers 12 and 14 are transcatheter intracardiac pacemakers which may be adapted for implantation wholly within a heart chamber, e.g., wholly within the RV, wholly within the left ventricle (LV), wholly within the RA or wholly within the left atrium (LA) of heart 8. In the examples described herein, the pacemaker system 10 is configured to sense cardiac electrical signals and cardiac mechanical signals and provide pacing therapy to a patient's heart 8. In particular, RV pacemaker 14 is configured to detect atrial events such as P-waves from a cardiac electrical signal received by RV pacemaker 14 and/or detect atrial mechanical events from a motion signal produced by a motion sensor included in RV pacemaker 14.

Pacemakers 12 and 14 are reduced in size compared to subcutaneously implanted pacemakers and may be generally cylindrical in shape to enable transvenous implantation via a delivery catheter. In the example of FIG. 1, RA pacemaker 12 is positioned along an endocardial wall of the RA, e.g., along the RA lateral wall or RA septum. RV Pacemaker 14 is positioned along an endocardial wall of the RV, e.g., near the RV apex though other locations are possible. The techniques disclosed herein are not limited to the pacemaker locations shown in the example of FIG. 1 and other positions and relative locations in the heart 8 and from each other are possible. For example, RV pacemaker 14 may alternatively be positioned in the LV and configured to detect cardiac signals and deliver atrial-synchronized ventricular pacing to the LV using the techniques disclosed herein. RA pacemaker 12 may be positioned outside or within the right atrium or left atrium to provide respective right atrial or left atrial sensing and pacing.

Pacemakers 12 and 14 are each capable of producing electrical stimulation pulses, e.g., pacing pulses, delivered to heart 8 via one or more electrodes on the outer housing of the respective pacemaker. RA pacemaker 12 is configured to deliver RA pacing pulses and sense a cardiac electrical signal from within the RA that may be used to produce an RA intracardiac electrogram (EGM) signal. RV pacemaker 14 is configured to deliver RV pacing pulses and sense an RV cardiac electrical signal using housing based electrodes for producing an RV EGM signal. The cardiac electrical signals may be sensed by the respective pacemaker 12 or 14 using housing based electrodes that are also used to deliver pacing pulses to the respective heart chamber.

In some examples, a patient may only require RV pacemaker 14 for delivering ventricular pacing. In other examples, depending on individual patient need, RA pacemaker 12 may be required for delivering atrial pacing. The RV pacemaker 14 is configured to control the delivery of ventricular pacing pulses to the ventricle in a manner that promotes synchrony between RA activation and RV activation, e.g., by maintaining a target AV pacing interval between atrial events and ventricular pacing pulses. RV pacemaker 14 starts an AV pacing interval upon detecting an atrial event signal from an atrial event input corresponding to atrial systole (intrinsic or paced) and delivers the ventricular pacing pulse upon expiration of the AV pacing interval to cause ventricular depolarization.

A target AV pacing interval may be a programmed value selected by a clinician and is the time interval from the detection of the atrial event until delivery of the ventricular pacing pulse. The target AV pacing interval may be identified as being hemodynamically optimal for a given patient based on clinical testing or assessments of the patient or based on clinical data from a population of patients. The target AV pacing interval may be determined to be optimal based on relative timing of electrical and/or mechanical events as identified from cardiac electrical signals and/or motion sensor signals. As described below, the target AV pacing interval may be adjusted based on the atrial event input used by a control circuit of RV pacemaker 14 for detecting the atrial events since the time of atrial event detection may be dependent on the type of atrial event input signal being used.

According to the techniques described herein, atrial events may be detected by RV pacemaker 14 from a motion sensor signal that includes motion signals caused by ventricular and atrial events. For example, acceleration of blood flowing into the RV through the tricuspid valve 16 between the right atrium and right ventricle caused by atrial systole, sometimes referred to as the "atrial kick," may be detected by RV pacemaker 14 from the signal produced by a motion sensor, for example an accelerometer, included in RV pacemaker 14.

Atrial events may be detected as far field atrial P-waves that are attendant to atrial depolarization may be detected by a control circuit of RV pacemaker 14 from the digitized cardiac electrical signal produced by a cardiac signal sensing circuit of RV pacemaker 14. Far-field P-waves are relatively low amplitude signals in the RV cardiac electrical signal, e.g., compared to the near-field R-wave, and therefore can be difficult to reliably detect at least some of the time. As such, atrial-synchronized ventricular pacing by RV pacemaker 14 may require alternative atrial event input signals.

For example, in some cases, detection of far-field atrial pacing pulse signals in the cardiac electrical signal produced by the cardiac signal sensing circuit of RV pacemaker 14 may provide more reliable atrial event detection than P-wave sensing or detection of atrial mechanical events from a motion sensor signal. In some instances, RV pacemaker 14 may be configured to switch from detecting P-waves in the cardiac electrical signal to detecting atrial mechanical events in the motion sensor signal or to detecting far-field atrial pacing pulses in the cardiac electrical signal when P-wave sensing is determined to be unreliable based on input switching criteria.

RA pacemaker 12 and RV pacemaker 14 may be configured to communicate directly with each other via a wireless communication link 24. When pacemakers 12 and 14 are configured to communicate with each other, communication may be minimized in order to conserve battery life of the intracardiac pacemakers 12 and 14. As such, wireless telemetric communication may not occur on a beat-by-beat basis between the RA pacemaker 12 and RV pacemaker 14 for communicating when the other pacemaker is sensing cardiac events or when it is delivering pacing pulses. As disclosed herein, however, intracardiac pacing system 10 may be configured to switch between atrial event inputs used by RV pacemaker 14 for detecting the timing of atrial events and setting AV pacing intervals. As described below, if atrial event detection from a sensor signal, e.g., from the cardiac electrical signal and/or from a motion sensor signal is lost or deemed unreliable, RV pacemaker 14 may switch the atrial event input used for detecting atrial events to atrial event signals that are broadcast by RA pacemaker 12 via communication link 24.

In the examples described herein, RA pacemaker 12 is a second implantable medical device configured to broadcast atrial event signals to RV pacemaker 14. In other examples, other implantable medical devices may be configured to broadcast atrial event signals to RV pacemaker 14, such as an implantable cardiac monitor capable of sensing P-waves, an ICD, or other device capable of sensing atrial event signals and broadcasting signals corresponding to the sensed atrial event signals.

Pacemakers 12 and 14 may each be capable of bidirectional wireless communication with an external device 20 for programming sensing and pacing control parameters used by the respective pacemaker 12 or 14 for sensing atrial and ventricular events and for controlling the timing of pacing pulse delivery. For example, pacemaker 14 may receive atrial event sensing control parameters, the AV pacing intervals and other pacing control parameters utilized for detecting the atrial events and for delivering atrial-synchronized ventricular pacing. Other programmed parameters may relate to input switching criteria used by RV pacemaker 14 for determining when to switch the atrial event input used for detecting atrial events and atrial event broadcasting criteria used by RA pacemaker 12 for determining when to broadcast atrial event signals to facilitate atrial event detection by RV pacemaker 14.

Different atrial event detection thresholds or parameters may be programmed for different atrial event inputs using programmer 20. A paced AV pacing interval may be programmed for use after paced atrial events, and a sensed AV pacing interval may be programmed for use after sensed intrinsic atrial events. Furthermore, different AV pacing intervals may be programmed for use with different atrial event inputs. As such, up to four different paced AV (PAV) pacing intervals and up to four different sensed AV (SAV) pacing intervals may be programmed when there are four different atrial event input signals available from which atrial events may be detected.

Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemakers 12 and 14. External device 20 may be located in a clinic, hospital or other medical facility. External device 20 may alternatively be embodied as a home monitor or a handheld device that may be used in a medical facility, in the patient's home, or another location.

External device 20 is configured for bidirectional communication with implantable telemetry circuitry included in RV pacemaker 14 and RA pacemaker 12. In some examples, external device 20 establishes a wireless radio frequency (RF) communication link 22 with RA pacemaker 12 and wireless RF communication link 26 with RV pacemaker 14 using a communication protocol that appropriately addresses the targeted pacemaker 12 or 14. Communication links 22, 24 and 26 may be established using an RF link such as BLUETOOTH®, Wi-Fi, Medical Implant Communication Service (MICS) or other communication bandwidth. External device 20 may include a programming head that is placed proximate pacemaker 12 or 14 to establish and maintain a communication link, and in other examples external device 20 and pacemakers 12 and 14 may be configured to communicate using a distance telemetry algorithm and circuitry that does not require the use of a programming head and does not require user intervention to maintain a communication link. An example RF telemetry communication system that may be implemented in system 10 is generally disclosed in U.S. Pat. No. 5,683,432 (Goedeke, et al.), hereby incorporated herein by reference in its entirety.

External device 20 may display data and information relating to pacemaker functions to a user for reviewing pacemaker operation and programmed parameters as well as EGM signals transmitted from RV pacemaker 14 or RA pacemaker 12, motion sensor signals acquired by RA pacemaker 14, or other physiological data that is acquired by and retrieved from pacemakers 12 and/or 14 during an interrogation session.

It is contemplated that external device 20 may be in wired or wireless connection to a communications network via a telemetry circuit that includes a transceiver and antenna or via a hardwired communication line for transferring data to a remote database or computer to allow remote management of the patient. Remote patient management systems including a remote patient database may be configured to utilize the presently disclosed techniques to enable a clinician to review EGM, motion sensor, and marker channel data and authorize programming of sensing and therapy control parameters in RA pacemaker 12 and/or RV pacemaker 14, e.g., after viewing a visual representation of EGM, motion sensor signal and marker channel data.

Figure 2A:
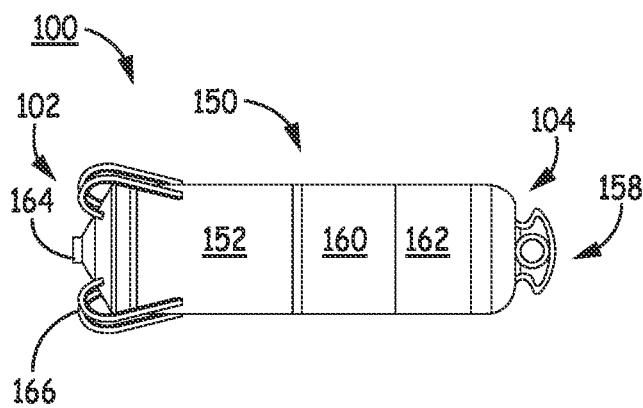
FIG. 2A is a conceptual diagram of an intracardiac pacemaker, which may correspond to the right atrial (RA) pacemaker or right ventricular (RV) pacemaker shown in FIG. 1.

FIG. 2A is a conceptual diagram of an intracardiac pacemaker 100, which may correspond to RA pacemaker 12 or RV pacemaker 14 shown in FIG. 1. Pacemaker 100 includes electrodes 162 and 164 spaced apart along the housing 150 of pacemaker 100 for sensing cardiac electrical signals and delivering pacing pulses. Electrode 164 is shown as a tip electrode extending from a distal end 102 of pacemaker 100, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 100 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac signal sensing circuitry, enclosed by housing 150 via an electrical feedthrough crossing housing 150. Electrode 162 may be formed as a conductive portion of housing 150 as a ring electrode that is electrically isolated from the other portions of the housing 150 as generally shown in FIG. 2A. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 100 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting cardiac mechanical events, e.g., atrial systolic events in RV pacemaker 14, and may be used for determining patient physical activity for providing rate responsive pacing.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by actively engaging with the endocardium or interacting with the ventricular trabeculae. Fixation tines 166 are configured to anchor pacemaker 100 to position electrode 164 in operative proximity to a targeted tissue for delivering therapeutic electrical stimulation pulses. Numerous types of active and/ or passive fixation members may be employed for anchoring or stabilizing pacemaker 100 in an implant position. Pacemaker 100 may include a set of fixation tines as disclosed in pending U.S. Publication No. 2012/0172892 (Grubac, et al.), hereby incorporated herein by reference in its entirety.

Pacemaker 100 may optionally include a delivery tool interface 158. Delivery tool interface 158 may be located at the proximal end 104 of pacemaker 100 and is configured to connect to a delivery device, such as a catheter, used to position pacemaker 100 at an implant location during an implantation procedure, for example within a heart chamber.

Figure 2B:
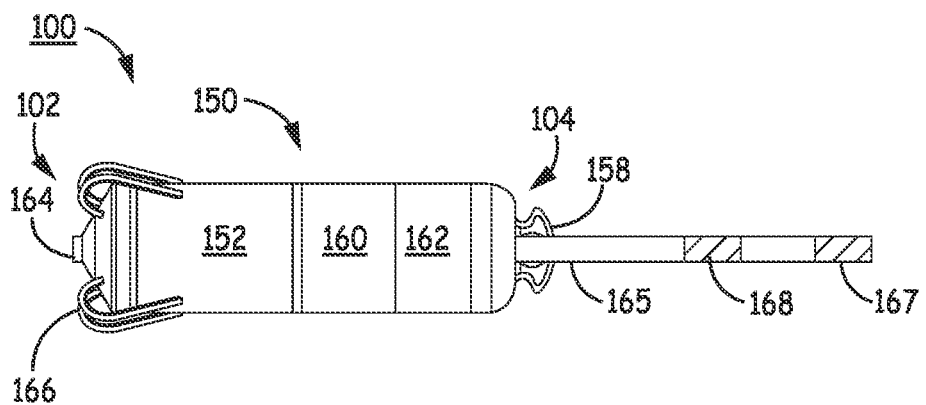
FIG. 2B is a conceptual diagram of another example of intracardiac pacemaker.

FIG. 2B is a conceptual diagram of another example of intracardiac pacemaker 100. In FIG. 2B, pacemaker 100 includes a proximal sensing extension 165 extending away from housing 150 and carrying one or more, in this case a pair, of sensing electrodes 167 and 168. The proximal sensing extension 165 may be coupled to the housing 150 for positioning a return sensing electrode 168 or 167 which may be paired with distal electrode 164 at an increased inter-electrode distance compared to the inter-electrode spacing of housing-based electrodes 162 and 164. The increased inter-electrode distance may facilitate sensing of far-field cardiac signals. For example, pacemaker 100 having sensing extension 165 may correspond to RV pacemaker 14 of FIG. 1. When distal end 102 is fixed along the RV apex, sensing extension 165 may extend toward the RA thereby positioning electrodes 167 and 168 nearer the atrial tissue for sensing far-field atrial P-waves. Electrode 164 may be used with an electrode 167 carried by sensing extension 165 for obtaining a cardiac electrical signal including far-field P-waves when pacemaker 100 is positioned in the RV. Alternatively, electrodes 167 and 168 may form a sensing electrode pair. One electrode 167 may be coupled to sensing circuitry enclosed in housing 150 via an electrical feedthrough crossing housing 150, and one electrode 168 may be coupled to housing 150 to serve as a ground electrode.

Figure 3:
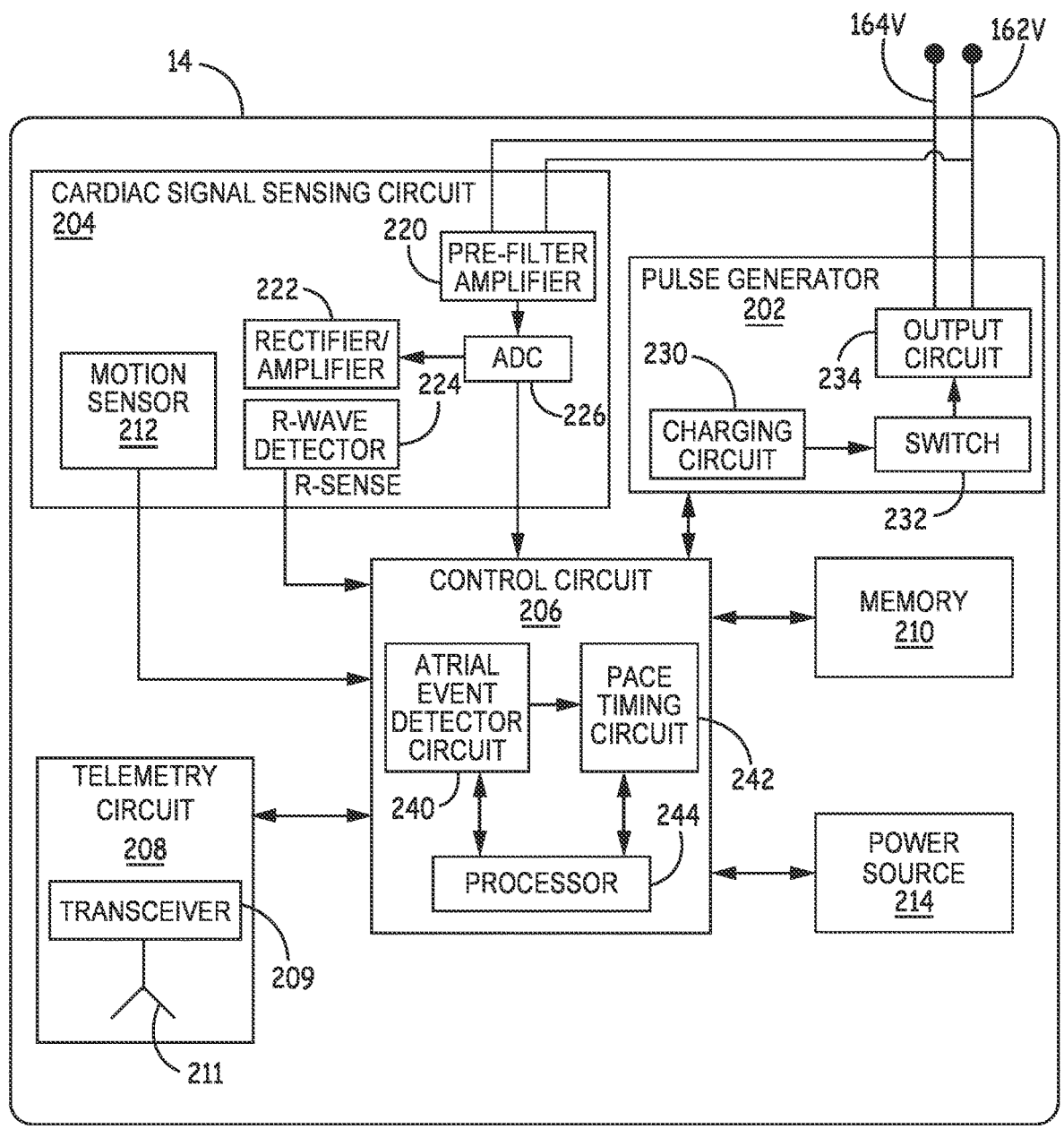
FIG. 3 is a schematic diagram of an example configuration of the RV pacemaker shown in FIG. 1.

FIG. 3 is a schematic diagram of an example configuration of RV pacemaker 14 shown in FIG. 1. In this example, RV pacemaker 14 includes a pulse generator 202, a cardiac signal sensing circuit 204, a control circuit 206, telemetry circuit 208, memory 210 and a power source 214. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Depiction of different features of RV pacemaker 14 as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial event detection from an atrial event input and ventricular pacing control operations performed by RV pacemaker 14 may be implemented in control circuit 206 executing instructions stored in memory 210 and relying on input from cardiac signal sensing circuit 204 and/or telemetry circuit 208. Providing software, hardware, and/or firmware to accomplish the described functionality in the context of any modern pacemaker, given the disclosure herein, is within the abilities of one of skill in the art.

Control circuit 206 includes an atrial event detector circuit 240, pace timing circuit 242, and processor 244 for performing the various functions attributed to control circuit 206 described herein. Control circuit 206 is configured to control pulse generator 202 to deliver atrial-synchronized ventricular pacing by setting an AV pacing interval in response to atrial event detector circuit 240 detecting an atrial event indicative of atrial systole. The atrial event is detected from a selected atrial event input received by atrial event detector circuit 240 from cardiac signal sensing circuit 204 or telemetry circuit 208. Control circuit 206 may selectively control which one of multiple atrial event inputs is used at any given time for detecting the atrial events to cause the AV pacing interval to be started.

Various atrial event input available for detection of atrial events by atrial event detector circuit 240 may include far-field P-waves included in a cardiac electrical signal received by sensing circuit 204 via electrodes 162V and 164V (and/or electrodes 167 and 168 when a sensing extension 165 is included as shown in FIG. 2B), atrial mechanical event signals included in a motion signal produced by motion sensor 212 of sensing circuit 204, far-field atrial pacing pulses included in a cardiac electrical signal received by sensing circuit 204, and broadcast atrial event signals received by telemetry circuit 208. Atrial event detector circuit 240 detects an atrial event from the selected atrial event input and passes an atrial event detection signal to pace timing circuit 242. Pace timing circuit 242 starts the AV pacing interval in response to the atrial event detection signal and controls pulse generator 202 to deliver a ventricular pacing pulse via electrodes 162V and 164V upon expiration of the AV pacing interval.

In this example, RV pacemaker 14 includes motion sensor 212 for producing a motion signal that includes atrial systolic mechanical event signals which can be detected by atrial event detector circuit 240. Motion sensor 212 may be implemented as an accelerometer; however, other motion sensors may be utilized successfully in pacemaker 14 for detecting atrial systolic mechanical events. Examples of motion sensors that may be implemented in pacemaker 14 include piezoelectric sensors and micro electro-mechanical systems (MEMS) devices. One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed in U.S. Pat. No. 4,485,813 (Anderson, et al.) and in U.S. Pat. No. 5,052,388 (Sivula, et al.), both of which patents are hereby incorporated by reference herein in their entirety.

Motion sensor 212 produces a motion signal that is correlated to motion or vibration of sensor 212 (and RV pacemaker 14), e.g., when subjected to flowing blood and cardiac motion as well as patient physical activity. Motion sensor 212 may be a one-dimensional, single axis accelerometer, two-dimensional or three-dimensional multi-axis accelerometer. Each axis signal may be analyzed individually or in combination for detecting atrial systolic events. Examples of three-dimensional accelerometers that may be implemented in RV pacemaker 14 and used for determining patient physical activity and detecting atrial mechanical systolic events for controlling ventricular pacing pulses using the presently disclosed techniques are generally described in U.S. Pat. No. 5,593,431 (Sheldon) and U.S. Pat. No. 6,044,297 (Sheldon), both of which are incorporated herein by reference in their entirety.

Cardiac signal sensing circuit 204 (also referred to herein simply as "sensing circuit" 204) is configured to receive a cardiac electrical signal via electrodes 162V and 164V by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in detecting far-field atrial P-waves or detecting far-field atrial pacing pulses. Sensing of far-field P-waves from the cardiac electrical signal received by control circuit 206 may be performed using methods generally disclosed in U.S. Pat. Publication No. 2016/0114169 A1 (Sheldon, et al.), published on Apr. 28, 2016, incorporated herein by reference in its entirety. The techniques disclosed herein, however, are not limited to a particular method or circuitry for detecting P-wave signals produced by cardiac signal sensing circuit 204 from the cardiac electrical signal received via electrodes 162V and 164V coupled to RV pacemaker 14 and passed to control circuit 206.

Sensing circuit 204 includes R-wave detector 224 for detecting R-waves from the cardiac electrical signal. The digital signal from ADC 226 may be passed to rectifier and amplifier circuit 222, which may include a rectifier, bandpass filter, and amplifier for passing a cardiac signal to R-wave detector 224. R-wave detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the R-wave detector 224 produces an R-wave sensed event signal (R-sense) that is passed to control circuit 206. In other examples, R-wave detector 224 may receive the digital output of ADC 226 for detecting R-waves by a comparator, morphological signal analysis of the digital EGM signal or other R-wave detection techniques. R-wave sensed event signals passed from R-wave detector 224 to control circuit 206 may be used for inhibiting a scheduled pacing pulse and for starting a ventricular lower rate (LR) pacing interval for maintaining a minimum ventricular pacing rate in the absence of detected atrial events.

The far-field P-waves or far-field atrial pacing pulses included the cardiac electrical signal received from sensing circuit 204 may be selected as the atrial event input used by atrial event detector circuit 240 for detecting atrial events. Control circuit 206 may select the atrial event input as a physiological atrial event input to be used by atrial event detector circuit 240 for detecting atrial events. For instance, control circuit 206 may select a physiological atrial event input by enabling atrial event detector circuit 240 to detect far-field atrial P-waves from the cardiac electrical signal received from ADC 226. In other instances, control circuit 206 may select a physiological atrial event input by enabling atrial event detector circuit 240 to detect atrial systolic mechanical events from the motion signal produced by motion sensor 212. These physiological atrial event inputs, P-wave signals or atrial systolic mechanical event signals, arise from a physiological source (e.g., atrial myocardial depolarization or atrial myocardial contraction) and do not require the RA pacemaker 12 to generate or broadcast an atrial event signal that is detected directly by atrial event detector circuit 240.

If atrial event detection from a physiological atrial event input is lost, or if other input switching criteria are met, control circuit 206 may control atrial event detector circuit 240 to use a different atrial event input for detecting atrial events. The atrial event input may be switched from a physiological atrial event input to a broadcast atrial event input. Broadcast atrial event input is signals produced by RA pacemaker 12 for direct detection by RV pacemaker 14. RV pacemaker 14 includes a receiver circuit for receiving broadcast atrial event input signals. In the example of FIG. 3, telemetry circuit 208 is one receiver circuit that is configured to receive broadcast atrial event signals in the form of wireless telemetry communication signals transmitted by RA pacemaker 12.

Cardiac signal sensing circuit 204 may also act as a receiver circuit for receiving broadcast atrial event signals in the form of far-field atrial pacing pulses. RA pacemaker 12 may broadcast atrial event signals by delivering atrial pacing pulses for pacing the atria and/or during the physiological refractory period following a P-wave. The atrial pacing pulses may be delivered at an increased atrial pacing pulse energy to increase the far-field atrial pacing pulse signal strength in the cardiac electrical signal received by electrodes 162V and 164V and passed to atrial event detector circuit 240.

As such, the term "receiver circuit" as used herein, refers to any circuit of RV pacemaker 14 that is configured to pass an atrial event input to control circuit 206 that includes atrial event signals that are received from and broadcast by RA pacemaker 12. The broadcast atrial event input signals are device-generated signals that are detected directly by RV pacemaker 14 as opposed to the physiological atrial event input signals which arise from the atria as physiological electrical or mechanical signals. Physiological atrial event input signals may be paced or intrinsic atrial events. In the case of paced atrial events, however, the physiological atrial event input signal is the evoked P-wave or the evoked atrial mechanical response to the atrial pacing pulse. The atrial pacing pulse is not detected directly by RV pacemaker 14 when the physiological atrial event input is selected. In contrast, when atrial event detector 240 is enabled to detect atrial events from a broadcast atrial event input of far-field atrial pacing pulses, the atrial pacing pulses are detected directly from the cardiac electrical signal received by sensing circuit 204 rather than detecting the electrical or mechanical evoked response of the atria to the delivered atrial pacing pulse. Detecting a paced atrial event from a physiological atrial event input may be thought of as an indirect detection of an atrial pacing pulse since the pacing-evoked P-wave or evoked mechanical event is detected but not the pacing pulse itself. The RV pacemaker 14, however, may be unable to distinguish between paced and sensed atrial events when using a physiological atrial event input.

Control circuit 206 may receive R-wave sensed event signals, digital cardiac electrical signals, and/or motion sensor signals from sensing circuit 204 for use in detecting and confirming cardiac events and controlling ventricular pacing. For example, R-wave sensed event signals may be passed to pace timing circuit 242 for inhibiting a scheduled ventricular pacing pulses and scheduling ventricular pacing pulses at a programmed ventricular LR pacing interval for preventing ventricular asystole in the absence of detected atrial events. The R-wave sensed event signals may also be received by atrial event detector circuit 240 for setting various blanking periods, refractory periods or sensing windows that are applied to an atrial event input for facilitating atrial event detection from the selected atrial event input.

Processor 244 may include one or more clocks for generating clock signals that are used by atrial event detector circuit 240 and by pace timing circuit 242 to control the timing of sensing windows, refractory periods, and for timing out a pacing escape interval that may be set to the AV pacing interval that is started upon atrial event detection. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242. As described below, the AV pacing interval may be set based on the atrial event input selected for atrial event detection.

Pace timing circuit 242 may additionally include an escape interval timer for timing out a ventricular LR pacing interval timer for controlling a minimum ventricular pacing rate. The LR pacing interval is started upon an R-wave sensed event signal or a delivered ventricular pacing pulse. If an atrial systolic event is not detected by atrial event detector circuit 240 during the LR pacing interval, a ventricular pacing pulse may be delivered by pulse generator 202 upon expiration of the LR pacing interval. The ventricular pacing pulse in this case is a non-atrial tracking or non-synchronous pacing pulse.

Processor 244 may retrieve other programmable pacing control parameters, such as pacing pulse amplitude and pacing pulse width that are used to control pulse generator 202 in generating pacing pulses. In addition to providing control signals to pace timing circuit 242 and pulse generator 202 for controlling pacing pulse delivery, processor 244 may provide sensing control signals to sensing circuit 204, e.g., R-wave sensing threshold control parameters, R-wave sensitivity, various blanking and refractory intervals applied to the cardiac electrical signal, and atrial event detection control signals to atrial event detector circuit 240 for use in detecting and confirming atrial events, e.g., in setting event detection windows, atrial refractory period, detection threshold amplitudes applied to the atrial event input signals, and any other atrial event detection criteria or parameters applied by circuitry included in atrial event detector circuit 240.

Pulse generator 202 generates electrical pacing pulses that are delivered to the right ventricle of the patient's heart via cathode electrode 164V and return anode electrode 162V. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or a LR pacing interval) and kept closed for a programmed pacing pulse duration to enable discharging of the holding capacitor of charging circuit 230. The holding capacitor, previously charged to the pacing pulse voltage amplitude, is discharged across electrodes 164V and 162V through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in RV pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to RV pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Power source 214 provides power to each of the other circuits and components of RV pacemaker 14 as required. Power source 214 may include one or more energy storage devices, such as one or more rechargeable or non-rechargeable batteries. The connections between power source 214 and other pacemaker circuits and components are not shown in FIG. 3 for the sake of clarity.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

Telemetry circuit 208 may be configured to at least receive wireless communication signals from RA pacemaker 12 and may be configured for bi-directional communication with RA pacemaker 12. In some instances, broadcast atrial event signals may be transmitted from RA pacemaker 12 to RV pacemaker telemetry circuit 208. Telemetry circuit 208 passes the atrial event signals to control circuit 206 for detection by atrial event detector circuit 240. Control circuit 206 may control telemetry circuit 208 to wake up to receive broadcast atrial event signals when control circuit 206 determines that input switching criteria are met and selects broadcast atrial event input for atrial event detector circuit 240. Telemetry circuit 208 may be powered up for receiving broadcast atrial event signals from RA pacemaker 12 until another atrial event input is selected for detecting atrial events.

The illustrative embodiments described herein include RA pacemaker 12 for producing broadcast atrial event signals. It is contemplated, however, that other implantable medical devices may broadcast atrial event signals. For example, a sensing-only device may be used to monitor for atrial P-waves and transmit atrial event signals to RV pacemaker 14. Another implantable medical device capable of broadcasting atrial event signals may be an intracardiac or extracardiac implantable device.

Figure 4:
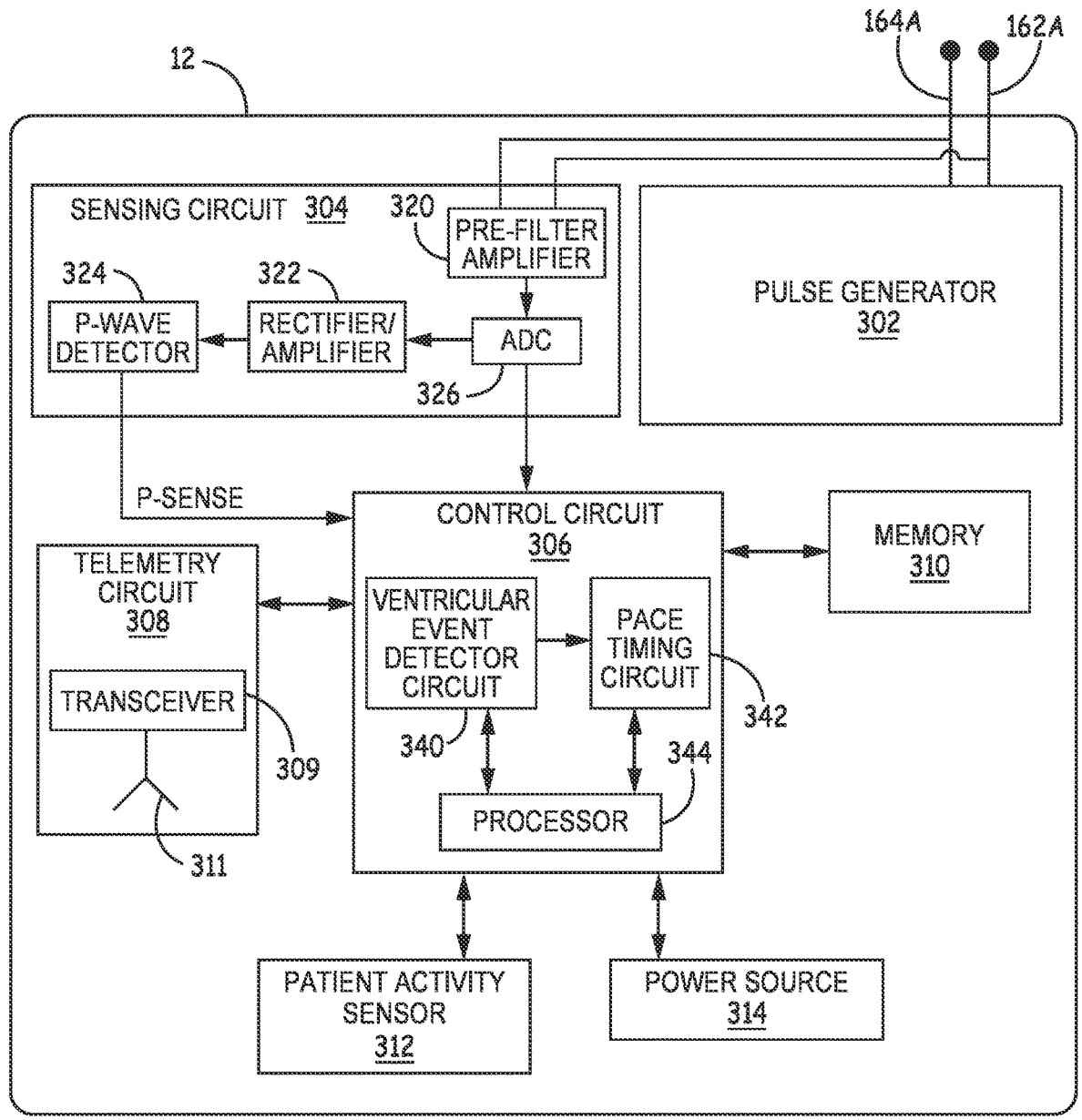
FIG. 4 is a schematic diagram of the RA pacemaker of FIG. 1 according to one example.

FIG. 4 is a schematic diagram of RA pacemaker 12 according to one example. RA pacemaker 12 includes pulse generator 302, sensing circuit 304, control circuit 306, telemetry circuit 308, memory 310, patient activity sensor 312, and power source 314. As described above in conjunction with FIG. 3, the various circuits represented in FIG. 4 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality. Providing software, hardware, and/or firmware to accomplish the described functionality of RA pacemaker 12 in the context of any modern pacemaker, given the disclosure herein, is within the abilities of one of skill in the art.

Control circuit 306 includes a ventricular event detector circuit 340, pace timing circuit 342, and processor 344 for performing the various functions attributed to control circuit 306 described herein. Control circuit 306 is configured to control pulse generator 302 to deliver atrial pacing pulses according to an atrial LR pacing interval in the absence of sensed, intrinsic atrial P-waves.

Sensing circuit 304 is configured to receive a cardiac electrical signal via electrodes 162A and 164A for sensing atrial P-waves and far-field ventricular R-waves. Sensing circuit 304 may include a pre-filter and amplifier circuit 320, ADC 326 and rectifier/amplifier 322 as generally described above in conjunction with FIG. 3. Components of sensing circuit 304 may be tuned to different filtering frequencies for optimizing P-wave and far-field R-wave sensing than sensing circuit 204, which is configured for providing a signal for near-field R-wave sensing and far-field P-wave sensing.

Sensing circuit 304 includes P-wave detector 324 for detecting P-waves from the rectified, filtered cardiac electrical signal by a sense amplifier or other detection circuitry that compares the incoming signal to a P-wave detection threshold, which may be an auto-adjusting threshold. When the incoming signal crosses the P-wave detection threshold, the P-wave detector 324 produces a P-wave sensed event signal (P-sense) that is passed to control circuit 306. P-wave sensed event signals passed to control circuit 306 may be used for inhibiting a scheduled atrial pacing pulse and re-starting an atrial LR pacing interval by pace timing circuit 342.

Control circuit 306 may receive P-wave sensed event signals and/or digital cardiac electrical signals from sensing circuit 204 for use in detecting and confirming cardiac events and controlling atrial pacing. Processor 344 may receive a patient activity sensor signal from sensor 312 for determining a patient activity metric and sensor indicated pacing rate (SIR). The LR pacing interval set by pace timing circuit 342 may be set according to the SIR to provide rate responsive pacing to the RA based on the patient's physical activity level.

Patient activity sensor 312 may be implemented as an accelerometer, which may be a piezoelectric accelerometer or a MEMS device. Processor 344 may adjust the LR pacing interval set by pace timing circuit 342 from a permanent LR pacing interval corresponding to a minimum atrial pacing rate to a temporary LR pacing interval to provide rate responsive pacing. The temporary LR pacing interval is set based on the SIR determined from the patient activity sensor signal to provide atrial pacing pulses at a rate greater than the minimum or base atrial pacing rate. The higher atrial rate support is provided according to the patient's metabolic demand during periods of non-resting physical activity based on the SIR. The use of an accelerometer in an intracardiac pacemaker for obtaining a patient activity signal is generally disclosed in pre-grant U.S. Pat. Publication No. 2015/0217119 A1 filed on Feb. 6, 2014 (Nikolski, et al.), incorporated herein by reference in its entirety. Examples of techniques for using a patient activity signal for determining a SIR and providing rate-responsive pacing are generally disclosed in U.S. Pat. No. 5,720,769 (van Oort) and U.S. Pat. No. 7,031,772 (Condie, et al.), both incorporated herein by reference in its entirety. Example techniques that may be implemented in an intracardiac pacemaker for providing rate responsive pacing based on patient activity are generally disclosed in pending U.S. Publication No. 2015/0217119, (Sheldon, et al.) and U.S. patent application Ser. No. 14/920, 228 filed Oct. 22, 2015 (Sheldon, et al.).

RA pacemaker 14 includes a ventricular event detector circuit 340 shown included control 306 in the example of FIG. 4 for detecting ventricular events, e.g., ventricular pacing pulses, evoked R-waves, and/or intrinsic R-waves. ADC 326 may pass a multi-bit, digital cardiac electrical signal to control circuit 306 for use by ventricular event detector circuit 340 in detecting far-field ventricular R-waves and/or far-field ventricular pacing pulses in some examples. Ventricular event detector circuit 340 may pass a ventricular event detection signal to processor 344 for determining a detected AV interval between a sensed P-wave or atrial pacing pulse and the subsequently detected ventricular event. Control circuit 306 monitors detected AV intervals for verifying that RV pacemaker 14 is delivering ventricular pacing pulses at an expected AV pacing interval as described in the timing diagrams and flow charts presented herein.

If ventricular events are not detected at the expected AV pacing interval, control circuit 306 may begin broadcasting atrial event signals. Control circuit 306 may control telemetry circuit 308 to begin transmitting atrial event signals to RV pacemaker 14 as wireless RF communication signals. Additionally or alternatively, control circuit 306 may broadcast atrial event signals by controlling pulse generator 302 to deliver atrial pacing pulses with a higher amplitude and/or pulse width to promote detection of atrial pacing pulses by atrial event detector 240 of RV pacemaker 14. In some cases, control circuit 306 may control pulse generator 302 to deliver a refractory pacing pulse, during the physiological refractory period of the atria following a P-wave as a broadcast atrial event signal. RV pacemaker 14 may switch from using a physiological atrial event input, such as P-wave signals or atrial mechanical event signals, to a broadcast atrial event input, e.g., wireless communication signals transmitted by telemetry circuit 308 or atrial pacing pulses delivered by pulse generator 302 and detected as far-field atrial pacing pulses by RV pacemaker 12. RA pacemaker 12 may be configured to recognize when RV pacemaker 14 has lost atrial event detection or switched to a broadcast atrial event input and operate to promote continuity of atrial event detection by RV pacemaker 14 by broadcasting atrial event signals.

Processor 344 may include one or more clocks for generating clock signals that are used by pace timing circuit 342 to control the timing of the LR atrial pacing interval. Pace timing circuit 342 may include one or more pacing escape interval timers or counters that are used to time out the LR pacing interval. Processor 344 may retrieve other programmable pacing control parameters, such as pacing pulse amplitude and pacing pulse width that are used to control pulse generator 302 in generating pacing pulses. In addition to providing control signals to pace timing circuit 342 and pulse generator 302 for controlling pacing pulse delivery, processor 344 may provide sensing control signals to sensing circuit 304, e.g., P-wave sensing threshold parameters, sensitivity, various blanking and refractory intervals applied to the cardiac electrical signal, and ventricular event detection control signals to ventricular event detector circuit 340 for use in detecting ventricular events and expected AV intervals for verifying atrial event detection by RV pacemaker 14 based on the expected timing of ventricular events following a most recent atrial event, paced or sensed.

Pulse generator 302 generates electrical pacing pulses that are delivered to the RA of the patient's heart via cathode electrode 164A and return anode electrode 162A. Pulse generator 302 may include a charging circuit, switching circuit and an output circuit as generally described above in conjunction with pulse generator 202 of FIG. 3 for generating and delivering atrial pacing pulses at timed LR intervals under the control of pace timing circuit 342.

Memory 310 may include computer-readable instructions that, when executed by control circuit 306, cause control circuit 306 to perform various functions attributed throughout this disclosure to RA pacemaker 14. The computer-readable instructions may be encoded within any non-transitory, computer-readable storage media listed above. RA pacemaker control circuit 306 and RV pacemaker control circuit 206 collectively operate as system control circuitry configured to determine when input switching criteria are met and controlling atrial event input used by RV pacemaker 14 for detecting atrial events to provide atrial-synchronized ventricular pacing.

Power source 314 provides power to each of the other circuits and components of RA pacemaker 12 as required. Power source 314 may include one or more energy storage devices, such as one or more rechargeable or non-rechargeable batteries. The connections between power source 314 and other pacemaker circuits and components are not shown in FIG. 4 for the sake of clarity.

Telemetry circuit 308 includes a transceiver 309 and antenna 311 for transferring and receiving data via a radio frequency (RF) communication link. Telemetry circuit 308 may be capable of bi-directional communication with external device 20 (FIG. 1) and RV pacemaker 14 as described above. Telemetry circuit 308 may be configured to at least transmit wireless communication signals from RA pacemaker 12 to RV pacemaker 14 for signaling RV pacemaker 14 when an atrial pacing pulse or sensed P-wave has occurred. Coded wireless transmission signals may be transmitted by telemetry circuit 308 to signal RV pacemaker when an intrinsic, sensed P-wave is detected and when an atrial pacing pulse has been delivered.

Figure 5:
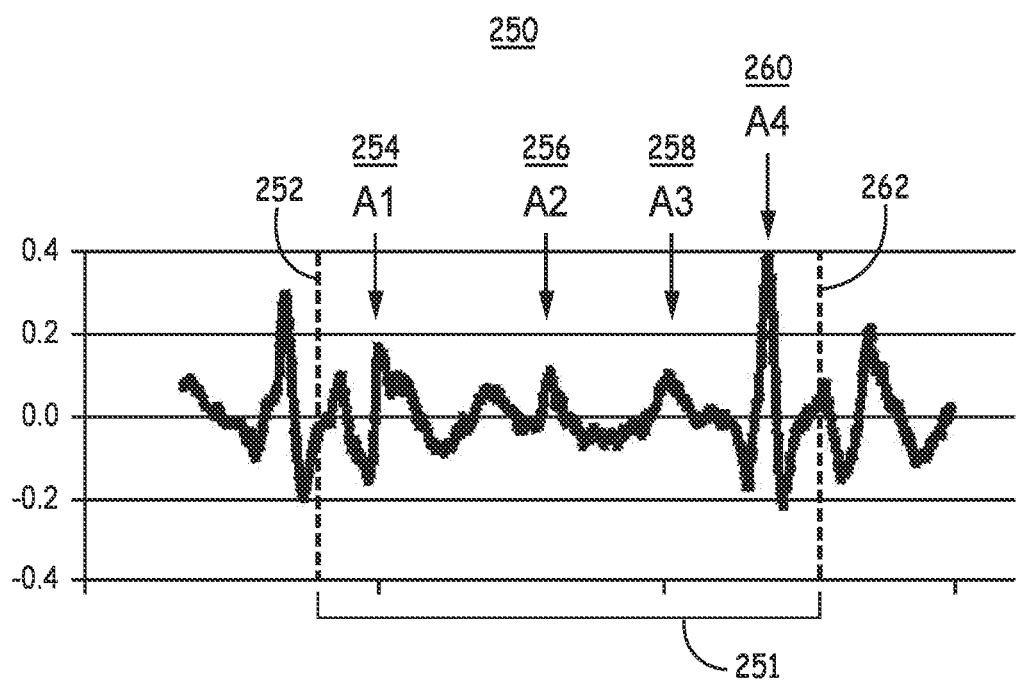
FIG. 5 is an example of a motion sensor signal that may be produced by a motion sensor of the RV pacemaker.

FIG. 5 is an example of a motion sensor signal 250 that may be produced by motion sensor 212 of RV cardiac signal sensing circuit 204 and passed to atrial event detector circuit 240 of RV pacemaker 14. The motion sensor signal 250 shown represents one ventricular cycle. Vertical dashed lines 252 and 262 denote the timing of two consecutive ventricular events (an intrinsic ventricular depolarization or a ventricular pace), marking the respective beginning and end of the ventricular cycle 251. The motion signal includes an A1 event 254, an A2 event 256, an A3 event 258 and an A4 event 260. The A1 event 254 is an acceleration signal that occurs during ventricular contraction and marks the approximate onset of ventricular mechanical systole. The A2 event 265 is an acceleration signal that occurs during ventricular relaxation and marks the approximate offset or end of ventricular mechanical systole. The A3 event 258 is an acceleration signal that occurs during passive ventricular filling and marks ventricular mechanical diastole. Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 is an atrial systolic mechanical event that may be detected by atrial event detector circuit 242 as an atrial event when the A4 events of motion sensor signal 250 are selected by RV pacemaker control circuit 206 as the atrial event input. The A4 event 260 may be detected from motion sensor signal 250 by atrial event detector circuit 240 for controlling pace timing circuit 242 to trigger ventricular pacing pulse delivery by starting the AV pacing interval in response to detecting the A4 event 260. Control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses.

The A1, A2, A3 and/or A4 events may be evaluated by control circuit 206 for determining the quality and reliability of motion sensor signal 250 for atrial event detection. One or more signal quality metrics based on the timing and/or morphology of the A1, A2, A3 and/or A4 events may be used in selecting an atrial event input by control circuit 206. In some examples, unacceptable A4 event signal quality may be an input switching criterion causing RV pacemaker 14 to switch the atrial event input. Atrial event detector circuit 240 of RV pacemaker 14 may be configured to detect the atrial event from the motion sensor signal 250 using techniques generally disclosed in U.S. Pat. Publication No. 2016/0023000 A1 (Cho, et al.), U.S. patent application Ser. No. 15/140,585 filed Apr. 28, 2016 (Ghosh, et al.), and U.S. patent application Ser. No. 15/280,538 filed on Sep. 29, 2016 (Splett, et al.,) and Ser. No. 15/280,339 filed on Sep. 29, 2016 (Sheldon, et al.), all of which are incorporated herein by reference in their entirety.

Figure 6:
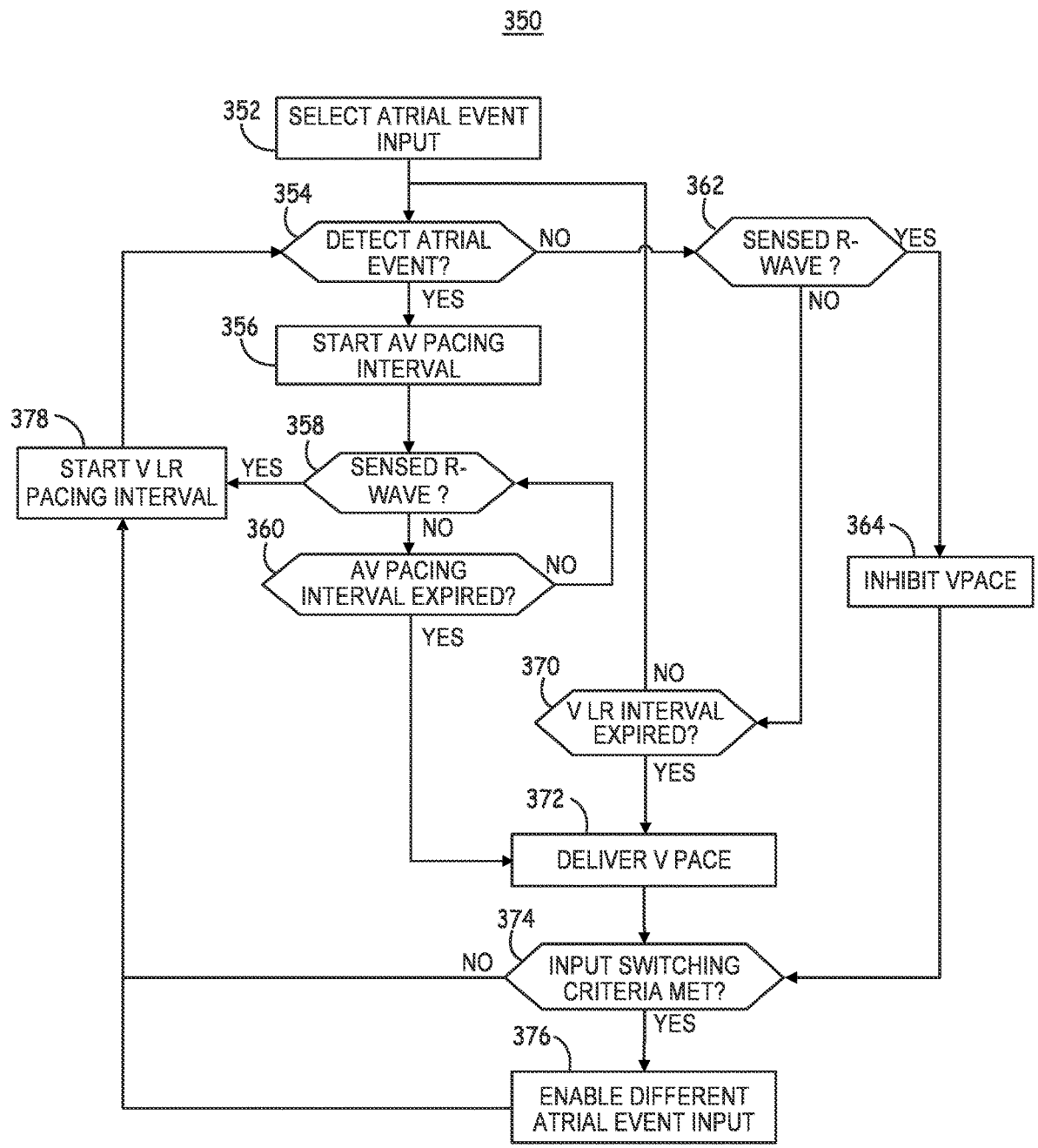
FIG. 6 is a flow chart of a method performed by the intracardiac pacing system of FIG. 1 for delivering atrial-synchronized ventricular pacing according to one example.

FIG. 6 is a flow chart 350 of a method performed by intracardiac pacing system 10 for delivering atrial-synchronized ventricular pacing according to one example. At block 352, an initial atrial event input is selected by control module 206 of RV pacemaker 14. The initial atrial event input may be far-field P-wave signals produced by RV pacemaker sensing circuit 204 in the cardiac electrical signal received via electrodes 162V and 164V and passed to control circuit 206. In other examples, the initial atrial event input may be A4 event signals, also referred to herein as "atrial systolic mechanical event signals" or simply "atrial mechanical event signals," in the motion signal produced by motion sensor 212, e.g., A4 event signals in motion sensor signal 250 shown in FIG. 5.

The atrial event input initially selected at block 352 may be a default atrial event input that RV pacemaker 14 is programmed to initially select. In other examples, the initial input may be selected based on an analysis of signal quality metrics of one or more cardiac signals. For instance, the reliability of P-wave sensing from the cardiac electrical signal received by RV sensing circuit 204 may be assessed by control circuit 206 by determining the P-wave amplitude, a ratio of P-wave to R-wave amplitude, a ratio of P-wave to T-wave amplitude, or other P-wave signal strength metric or combination of metrics. The motion signal received from motion sensor 212 may be evaluated to determine if atrial systolic mechanical event signals can be reliably detected based on the amplitude and/or timing of the atrial systolic event signal and/or the amplitude and/or timing of ventricular mechanical event signals included in the motion signal.

The signal quality analysis for determining if atrial event detection is reliable may be performed on a first atrial event input, and if acceptable the first atrial event input may be selected. If not acceptable, control circuit 206 may analyze the signal quality of a second atrial event input for reliable atrial event detection. In other examples, two or more available atrial event inputs may be evaluated and the input having the highest signal quality for atrial event detection, e.g., the signal with the greatest atrial event signal strength relative to signal baseline and ventricular events, may be selected as the initial atrial event input.

In other examples, the selection of an initial atrial event input may be based at least in part on a patient condition, such as the paced or intrinsic atrial heart rate, patient physical activity level and/or patient body posture. Reliability of P-wave sensing from the cardiac electrical signal and/or atrial systolic mechanical event detection from the motion sensor signal may be posture dependent in some patients. Detection of physiological atrial events may be relatively more challenging when the heart rate is elevated. Detection of A4 events from the motion sensor signal may be more challenging when patient physical body movement produces increased motion signals in the motion sensor signal. Detection of P-waves and A4 events may be confounded by increased heart rate when the timing between T-waves and P-waves or ventricular mechanical diastolic events and atrial mechanical systolic events becomes shorter or even fused.

As such, the patient's heart rate, physical activity and/or body posture may be determined at block 352 and contribute to the initial atrial event input selection according to which input is expected to provide acceptable atrial event detection. Patient physical activity and posture detection may be determined from the motion sensor signal received from sensor 212 using techniques generally described in the above-incorporated U.S. Pat. No. 5,593,431 (Sheldon) and U.S. Pat. No. 6,044,297 (Sheldon). During this process of selecting the initial atrial event input, for example upon initial implantation of RA pacemaker 12 and RV pacemaker 14, RA pacemaker 12 may temporarily broadcast atrial event signals to enable RV pacemaker 14 to confirm P-wave and/or A4 event detections and determine the atrial rate for contributing to the atrial event input selection. RV pacemaker control circuit 206 may determine the patient's physical activity and/or body posture from the motion sensor signal received from motion sensor 212. If the heart rate and/or patient physical activity exceed respective thresholds and/or patient posture is identified as a poor condition for using a physiological atrial event input, the initial atrial event input may be selected as a broadcast atrial event input.

Generally, powering RV pacemaker telemetry circuit 208 to receive broadcast atrial event signals and powering RA pacemaker telemetry circuit 308 to broadcast the atrial event signals on a beat-by-beat basis, or nearly beat-by-beat basis, requires greater power consumption than detecting physiological atrial events from the cardiac electrical signal or the motion sensor signal. In order to detect atrial pacing pulses as broadcast atrial events from the cardiac electrical signal received by RV pacemaker 14, the atrial pacing pulse energy delivered by RA pacemaker 12 may need to be increased and/or extra refractory pacing pulses may be delivered, which increases power consumption by RA pacemaker 12.

As such, a physiological atrial event input selected at block 352 may be more power efficient for the overall system 10 than an atrial event input that relies on broadcast atrial event signals generated by RA pacemaker 12. The initial atrial event input signal may therefore preferentially be a physiological atrial event input rather than a broadcast atrial event input that may require greater power consumption in the overall pacing system 10. In some cases, however, e.g., during initial operation of the system 10, in the presence of electrical signal or motion sensor signal noise, high heart rate, high patient activity, or a detected patient body posture known to be associated with poor physiological atrial event detection, a broadcast atrial event input may be selected as the input at block 352 to promote reliable atrial event detection and proper timing of ventricular pacing pulses.

After selecting an atrial event input, atrial event detector circuit 240 waits for an atrial event detection at block 354. If an atrial event is detected, pace timing circuit 242 starts an AV pacing interval at block 356. If an R-wave is sensed by sensing circuit 204 at block 358 before expiration of the AV pacing interval (block 360), the scheduled ventricular pacing pulse is withheld. Pace timing circuit 242 starts a ventricular LR pacing interval at block 378 in response to the sensed R-wave.

If the AV pacing interval expires without sensing an R-wave, the scheduled ventricular pacing pulse is delivered by pulse generator 202 at block 372. Control circuit 202 may determine if input switching criteria are met at block 374. Generally, if the atrial event is detected and the ventricular pacing pulse delivered, it is expected that the selected atrial event input is reliable for continuing using the selected input for atrial event detection. As such, the determination at block 374 may not be performed when the ventricular pacing pulse is delivered at block 372 upon expiration of the AV pacing interval.

In some cases, however, a change in patient activity, patient posture, or atrial rate may be condition for causing the atrial event input to be switched to another input considered to be more reliable under the present patient condition(s). As such, the atrial event rate, patient physical activity level, patient body posture or other patient condition may be determined at block 374 for determining if input switching criteria are met. If input switching criteria are not met, the process returns to start the ventricular LR pacing interval at block 378 in response to delivering the ventricular pacing pulse. If input switching criteria are met at block 374, a different atrial event input is selected at block 376.

If an atrial event is not detected at block 354 before an R-wave is sensed at block 362, the AV interval is not started. If an R-wave is sensed at block 362, before the ventricular LR pacing interval expires (block 370) and before an atrial event is detected (block 354), the ventricular pacing pulse is inhibited block 364. At block 374, control circuit 206 determines if the input switching criteria are met. If an atrial event is not detected and an R-wave is not sensed ("no" branch of block 362) and the ventricular LR pacing interval expires (block 370), a ventricular pacing pulse is delivered at block 372. A ventricular pacing pulse is delivered at the ventricular LR pacing interval to prevent ventricular asystole. After delivering the ventricular pacing pulse, control circuit 206 determines if the input switching criteria are met at block 374.

Input switching criteria may be satisfied at block 374 if atrial events are not detected for a predetermined number of consecutive or non-consecutive ventricular cycles. In other words, if a predetermined number of ventricular pacing pulses are delivered at the ventricular LR pacing interval and/or R-waves are sensed prior to expiration of the ventricular LR pacing interval, the atrial event detection may be deemed unreliable and the input switching criteria may be satisfied. For example, if 3 out of 5, 6 out of 8, 12 out 15 or other threshold number of consecutive or non-consecutive ventricular cycles occur without detecting the atrial event out of a predetermined number of consecutive ventricular cycles, the input switching criteria may be satisfied at block 374. Atrial event input is switched at block 376 in response to the input switching criteria being met. The atrial event input is switched by enabling atrial event detector circuit 240 to detect of atrial events from different input signals.

For example, atrial event detector circuit 240 may be receiving the cardiac electrical signal from sensing circuit 204 for sensing far-field P-waves and switch to receiving the motion signal from motion sensor 212 for detecting atrial systolic mechanical event signals at block 376 or vice versa. Atrial event detector circuit 240 may switch from sensing P-waves or from sensing atrial systolic mechanical events to receiving atrial event communication signals from telemetry circuit 208. In other instances, atrial event detector circuit 240 switches from a current atrial event input to detecting far-field atrial pacing pulses from the cardiac electrical signal passed to control circuit 206, e.g., a signal produced by ADC 226 of sensing circuit 204.

Enabling a different atrial event input at block 376 may include actions taken by RA pacemaker 12 in addition to switching the atrial event input used by atrial event detector circuit 240 of RV pacemaker 14. As such, RA pacemaker 12 may be configured to monitor for atrial event broadcasting criteria being met at block 374 to enable RA pacemaker 12 to recognize when RV pacemaker 14 is switching between atrial event inputs. Recognition of the RV pacemaker 14 switching to a different atrial event input by RA pacemaker 12 enables RA pacemaker 12 to initiate broadcasting of atrial event signals by RA pacemaker telemetry circuit 308, by increasing atrial pacing pulse energy delivered by RA pacemaker pulse generator 302, and/or by delivering refractory atrial pacing pulses to facilitate detection of atrial events by atrial event detector circuit 240. It is recognized that in some cases, an increased atrial pacing pulse energy is not required for RV pacemaker 14 to detect the atrial pacing pulses.

Figure 7:
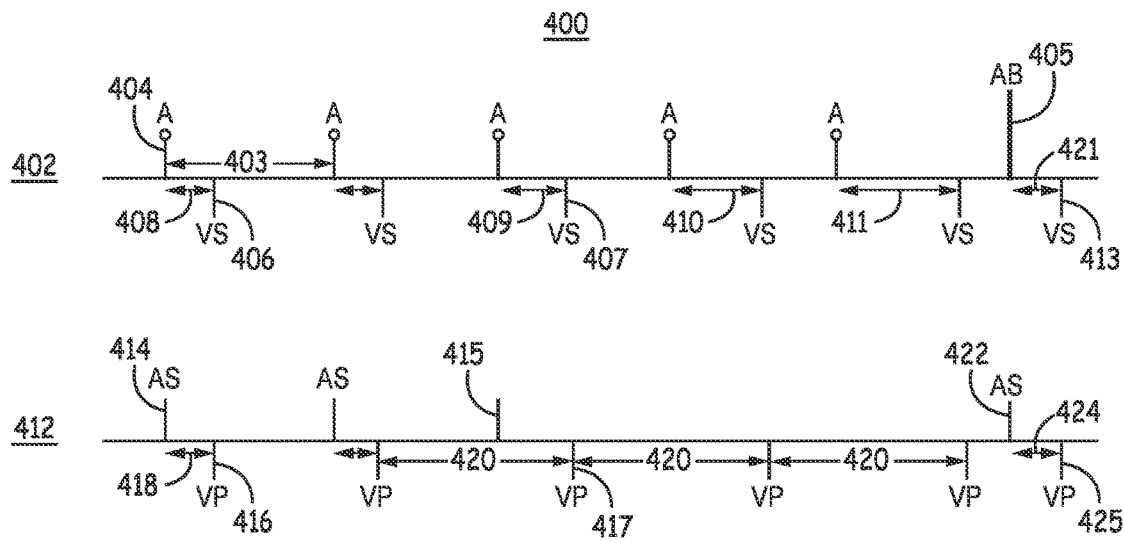
FIG. 7 is a timing diagram depicting cardiac events that are sensed by the RA pacemaker and the RV pacemaker of FIG. 1 during ventricular pacing.

FIG. 7 is a timing diagram 400 depicting cardiac events that are sensed by RA pacemaker 12 and RV pacemaker 14 during ventricular pacing. Timeline 402 depicts atrial events (A) 404 occurring at a stable atrial rate interval 403. The atrial events 404 may be intrinsic P-waves sensed by sensing circuit 304 of RA pacemaker 12, or the atrial events 404 may be atrial pacing pulses delivered by RA pacemaker pulse generator 302 at an atrial LR pacing interval set at a permanent LR interval or a SIR based on patient physical activity. RA pacemaker 12 senses ventricular events (VS) 406 at a detected AV interval 408 that matches an expected AV pacing interval 418 set by RV pacemaker pace timing circuit 242.

Timeline 412 depicts ventricular pacing pulses (VP) 416 and detected atrial events (AS) 414 that are detected by atrial event detector circuit 240. Atrial events 414 may be detected as P-waves from the cardiac electrical signal produced by RV pacemaker sensing circuit 204 or as A4 events detected from a motion sensor signal produced by motion sensor 212. Pace timing circuit 242 sets the AV pacing interval 418 in response to detecting the atrial events 414 and delivers the ventricular pacing pulse 416 upon expiration of AV pacing interval 418 (in the absence of a sensed R-wave). The ventricular pacing pulse 416, or the subsequently evoked R-wave, is detected by RA pacemaker 12 as VS event 406 at the detected AV interval 408, which matches the expected AV pacing interval 418.

Atrial event detection is lost by RV pacemaker 14 when an expected atrial event 415 is not detected by atrial event detector circuit 240. RV pacemaker 14 controls the pulse generator 202 to deliver a ventricular pacing pulse 417 at the ventricular LR pacing interval 420 following the preceding pacing pulse in the absence of a detected atrial event. RA pacemaker 12 detects the ventricular event 407 at a detected AV interval 409, which is greater than the expected AV pacing interval 418.

In the example shown, three ventricular pacing pulses are delivered at the ventricular LR pacing interval 420 in the absence of detected atrial events. The corresponding detected AV intervals 409, 410 and 411 are determined by RA pacemaker 12 between respective atrial events and sensed ventricular events 407. These detected AV intervals 409, 410 and 411 are progressively increasing. In the example shown the ventricular pacing pulses 417 delivered at the ventricular LR interval 420 occur at a slower rate than the atrial rate resulting in a progressively increasing detected AV interval 409, 410 and 411. In some examples, RV pacemaker control circuit 206 may be configured to deliver the ventricular pacing pulses using a rate smoothing algorithm in the absence of detected atrial events. As such, the first ventricular pacing pulse 417 may be delivered later than the expected atrial event 415 but earlier than the programmed ventricular LR interval. Subsequent ventricular pacing pulses may be delivered at progressively increasing LR intervals to gradually adjust the ventricular rate from the atrial-tracking rate to the programmed ventricular rate. In this case, the detected AV intervals 409, 410, and 411 will progressively increase as the ventricular pacing interval is increased according to a rate smoothing algorithm.

RA pacemaker control circuit 306 may be configured to produce broadcast atrial event signals in response to a threshold number of unexpected detected AV intervals. The threshold number may be one or more unexpected detected AV intervals, which may be consecutive or non-consecutive detected AV intervals. In the example shown, RA pacemaker 12 enables an atrial event broadcast mode by broadcasting atrial event 405 after three unexpected detected AV event intervals 409, 410, and 411, though another threshold number of unexpected detected AV intervals may be used.

The broadcast atrial event 405 is detected as AS event 422 by the atrial event detector 240 of RV pacemaker 14, causing the AV pacing interval 424 to be set for delivering the next ventricular pacing pulse 425. RA pacemaker 12 senses the ventricular pacing pulse (or the subsequently evoked R-wave) as VS event 413 at the expected detected AV interval 421. Control circuit 306 of RA pacemaker 12 determines that atrial event detection by RV pacemaker 14 is restored based on the expected detected AV interval 421. If the atrial broadcast event 405 is not followed by an expected detected AV interval 421, RA pacemaker 12 may increase the strength of the broadcast atrial event 405 or change the type of broadcast atrial event signal until restoration of atrial event detection by RV pacemaker 14 is recognized based on one or more expected detected AV intervals.

The AV pacing interval 424 and expected detected AV interval 421 may be the same as the original AV pacing interval 418 and expected detected AV interval 408, respectively, but may be different intervals. RV pacemaker control circuit 206 may set a different AV pacing interval 424 in response to detecting atrial event 422 from a broadcast atrial event input than the AV pacing interval 418 set in response to detecting atrial event 414 from a physiological atrial event input. The AV pacing interval 424 may be adjusted to be different than AV pacing interval 418 to account for a difference in timing of the detected atrial events 414 and 422 relative to the actual, corresponding atrial events. For example, an inherent system delay may be present in detecting broadcast atrial event signal 405 compared to detecting a physiological atrial event input signal. After switching to the broadcast atrial event input, RV pacemaker 14 may adjust the AV pacing interval 418 according to which broadcast signal is being used as the atrial event input. For instance, when the atrial event is detected by receiving a broadcast wireless communication signal 405 by telemetry circuit 208, pace timing circuit 242 may set the AV pacing interval 424 to be 10 to 50 ms shorter than the AV pacing interval 418 used when the atrial event is detected as a P-wave from the cardiac electrical signal. If the atrial event input is initially the A4 event signals of the motion sensor signal, the AV pacing interval 424 may be set longer than the AV pacing interval 418. A relatively short AV pacing interval 418 may be set following an A4 event detection, e.g., 50 ms, which occurs later than the atrial electrical events. If broadcast atrial event 405 is a delivered atrial pacing pulse, the AV pacing interval 424 may be longer than AV pacing interval 418, e.g., increased from 50 ms to 200 ms.

Different AV pacing intervals may be used when the atrial events are being detected from different physiological atrial event inputs and when the atrial events are being detected from different broadcast atrial event inputs. A physiological time delay is expected between an atrial pacing pulse and a sensed P-wave and between the sensed P-wave and the atrial mechanical contraction. As such, the AV pacing interval used by pace timing circuit 242 may be selected based on the atrial event input being used by atrial event detector circuit 240 to account for physiological time delays and/or intracardiac pacemaker system time delays that may exist in detecting broadcast atrial event signals.

The atrial broadcast event 405 may be a wireless communication signal transmitted by RA pacemaker telemetry circuit 308 upon sensing an atrial P-wave by sensing circuit 304 or upon delivering an atrial pacing pulse by pulse generator 302. In this case, the detected atrial event 422 is wireless atrial event communication signal received by RV pacemaker telemetry circuit 208 that is passed to atrial event detector circuit 240 (or directly to pace timing circuit 242). RV pacemaker 14 may be configured to switch the atrial event input to broadcast communication signals received from RA pacemaker telemetry circuit 308 via RV pacemaker telemetry circuit 208 in response to a threshold number of ventricular cycles paced at the ventricular LR pacing interval without atrial event detections. The threshold number of paced ventricular cycles at the LR pacing interval may or may not be required to be consecutive.

In the example of FIG. 7, RV pacemaker telemetry circuit 208 is enabled to receive communication signals in response to three consecutive ventricular pacing pulses delivered at the ventricular LR pacing interval (or rate smoothing intervals). The threshold number of lost atrial event detections required for input switching criteria to be met in RV pacemaker 14 may or may not be the same as the threshold number of unexpected detected AV intervals required for RA pacemaker 12 to enable broadcast atrial event signals. Control circuit 206 may enable telemetry circuit 208 to be powered up to a listening mode for receiving atrial event broadcast signals from the RA telemetry circuit 308.

In another example, the atrial broadcast event 405 may be an atrial pacing pulse that is delivered at an increased pacing pulse amplitude and/or pulse width. Atrial events 404 may be atrial pacing pulses that are delivered at a safety margin greater than an atrial pacing capture threshold. In response to a threshold number of unexpected detected AV intervals, e.g., intervals 409, 410 and 411, RA pacemaker control circuit 306 may increase the RA pacing pulse energy by controlling pulse generator 302 to deliver pacing pulses with a pulse amplitude and/or pulse width that is greater than the pulse amplitude and/or width normally used to deliver atrial pacing pulses when RA pacemaker 12 is not broadcasting atrial event signals.

In some examples, the atrial pacing pulses may not be required to be increased in order to be detected by RV pacemaker 14. In this case, the broadcast atrial event signal may be a double pacing pulse, one to capture the atria and a second refractory pacing pulse to signal RV pacemaker 14 that the atrial event is a paced event. A single refractory pacing pulse may be delivered by RA pacemaker 12 as a broadcast atrial event when an intrinsic P-wave is sensed to signal RV pacemaker 14 that the atrial event is a sensed event.

RV pacemaker control circuit 206 may switch the atrial event input by enabling atrial event detector circuit 240 to detect far-field atrial pacing pulses from the cardiac electrical signal produced by sensing circuit 204. Example techniques for detecting pacing pulses from a cardiac electrical signal are generally disclosed in pending U.S. Publication No. 2016/0250478 (Greenhut, et al.) and U.S. patent application Ser. No. 14/826,396 filed Aug. 14, 2015 (Gunderson, et al.), both incorporated herein by reference in its entirety.

RA pacemaker control circuit 306 may determine whether to broadcast atrial event signals as wireless telemetry communication signals or by delivering atrial pacing pulses (at a higher pacing pulse energy and/or refractory pacing pulses) or a combination of both communication signals and pacing pulses during the atrial event broadcast mode. If the atrial rhythm is a paced rhythm at the time that atrial event detection by RV pacemaker 14 is determined to be lost by RA pacemaker 12, RA pacemaker 12 may broadcast atrial events by delivering the atrial pacing pulses at the same or an increased pulse energy. If the atrial rhythm is a sensed rhythm at the time that atrial event detection by RV pacemaker 14 is lost, RA pacemaker 12 may broadcast the time of the sensed atrial events by transmitting a wireless communication signal via telemetry circuit 308 or by delivering refractory pacing pulses. In some examples, RA pacemaker 12 broadcasts atrial event signals using a combination of pacing pulses and wireless communication signals transmitted by telemetry circuit 308. Atrial pacing pulses, when delivered, may be delivered at the normal or increased pacing pulse energy to signal paced atrial events. If a P-wave is sensed, the atrial event signal may be broadcast by the telemetry circuit 308. In this case, RV pacemaker 14 enables atrial event detector circuit 240 to monitor for both far-field atrial pacing pulses in the cardiac electrical signal received from sensing circuit 204 and for wireless communication signals received by RV pacemaker telemetry circuit 208.

In some examples, RV pacemaker control circuit 206 may enable atrial event detector circuit 240 to switch from one physiological atrial event input to another physiological atrial event input, if available, before relying on a broadcast atrial event input, which may require greater power consumption by one or both of pacemakers 12 and 14 than use of a physiological atrial event input. For instance, RV pacemaker 14 may initially select P-wave sensing from the cardiac electrical signal as the atrial event input. If P-wave sensing is lost for a threshold number of ventricular cycles, RV pacemaker 14 may switch to A4 event detection from the motion sensor signal as the atrial event input. Both of these atrial event inputs and atrial event detection methods do not require RA pacemaker 12 to alter its operation. Atrial event signals that are selected as atrial event input without requiring RA pacemaker 12 to alter its operation are referred to herein as "physiological" atrial event input signals. The physiological atrial event signals arise from a physiological source as opposed from originating from the RA pacemaker 12 as a device-generated atrial event signal. If atrial event detection is not restored after switching from one physiological atrial event input to another physiological atrial event input, e.g., from P-wave signals to atrial mechanical event signals or vice versa, RV pacemaker 14 may enable atrial event detection using broadcast atrial event input originating from RA pacemaker 12.

RV pacemaker 14 may switch from a first physiological atrial event input to a second physiological atrial event input in response to a first threshold number of ventricular cycles without atrial event detections. If a second threshold number of ventricular cycles occur without atrial event detections after switching the second physiological atrial event input, RV pacemaker 14 may switch atrial event input used by atrial event detector circuit 240 from the second physiological atrial event input to a broadcast atrial event input. RA pacemaker 12 may be configured to enable atrial event broadcasting in response to the second threshold number of unexpected detected AV intervals. In other examples, RA pacemaker 12 may be enabled to broadcast atrial event signals when a third threshold number of unexpected detected AV intervals is detected that is intermediate the first and second thresholds used by RV pacemaker 14. In this way, by the time RV pacemaker 14 switches the broadcast atrial event input, RA pacemaker 12 will already be broadcasting atrial event signals for immediate detection by RV pacemaker 14.

Figure 8:
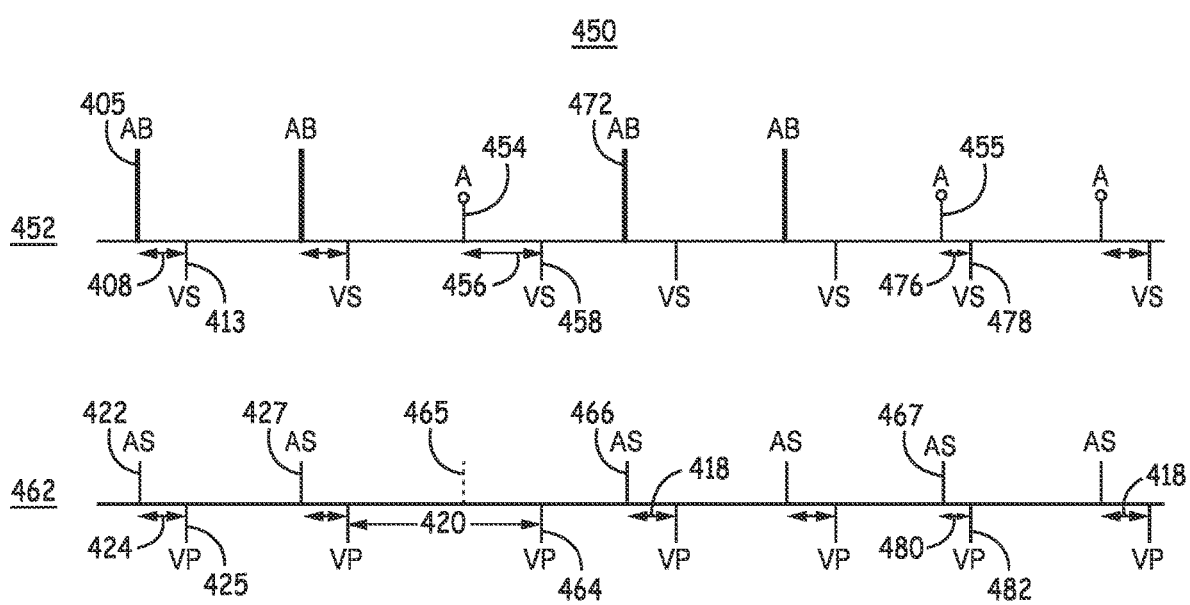
FIG. 8 is a timing diagram of atrial events and ventricular events produced and detected by the intracardiac pacemaker system of FIG. 1.

FIG. 8 is a timing diagram of atrial events and ventricular events produced and detected by intracardiac pacemaker system 10. Timeline 452 depicts events produced and detected by RA pacemaker 12. Timeline 454 depicts events produced and detected by RV pacemaker 14. RA pacemaker 12 is operating in an atrial event broadcast mode, producing broadcast atrial event signals 405. As described above in conjunction with FIG. 7, atrial event detector circuit detects the broadcast atrial events 405 and produces an atrial event sense signal (AS) 422. Pace timing circuit 242 starts an AV pacing interval 424 and controls pulse generator 202 to deliver a pacing pulse 425 at the expiration of AV pacing interval 424. RA pacemaker 12 detects the ventricular pacing pulse (or the evoked R-wave) and as indicated by VS event 413 at the expected detected AV interval 421.

RA pacemaker control circuit 306 may be configured to periodically withhold an atrial event broadcast signal to determine if atrial event detection by RV pacemaker 14 using a physiological atrial event input has returned. The atrial event 454 may be an atrial pacing pulse that is delivered at normal pacing pulse energy, e.g., at a safety margin greater than a determined atrial pacing capture threshold. In other instances, atrial event 454 may be a sensed P-wave. A broadcast atrial event signal indicating the time of atrial event 454 is withheld by RA pacemaker 12.

In this example, atrial event detection by RV pacemaker 14 may be switched to a physiological atrial event input after detecting the Nth atrial event 427 using a broadcast atrial event input. The expected atrial event detection 465 does not occur; atrial event detection using the physiological atrial event input has not returned. As a result, the ventricular LR pacing interval 420 expires without an atrial event detection, and a ventricular pacing pulse 464 is delivered. The ventricular pacing pulse 464 (or an evoked far-field R-wave) is detected by RA pacemaker 12 as VS event 458 at an unexpected detected AV interval 456. Since the detected AV interval does not match the expected AV pacing interval 424, RA pacemaker 12 may return to an atrial event broadcast mode on the next atrial cycle, as indicated by broadcast atrial event 472. In other examples, the broadcast atrial event may be withheld for multiple atrial cycles to enable RV pacemaker 14 to attempt atrial event detection on more than one ventricular cycle, perhaps using more than one physiological atrial event input or by adjusting physiological atrial event detection parameters.

After a predetermined number of atrial event broadcast signals, e.g., two or more broadcast signals, RA pacemaker 12 withholds the atrial event broadcast signal again and RV pacemaker 14 switches to a physiological atrial event input. This time, RV pacemaker 14 detects the atrial event 455 and produces an atrial sense event signal 467. RV pacemaker 14 may be programmed to switch from a broadcast atrial event input to a physiological atrial event input after detecting a predetermined number of broadcast atrial events so that the RA pacemaker 12 and the RV pacemaker 14 are coordinated to respectively terminate broadcasting atrial event signals and switch to a physiological atrial event input on the same cardiac cycle(s).

RA pacemaker 12 detects a ventricular event 478 at a detected AV interval 476 that meets expected detected AV interval criteria, confirming that detection of atrial events by RV pacemaker 14 has been restored. RA pacemaker 12 terminates the atrial event broadcast mode and continues delivering atrial pacing pulses at the normal pacing pulse energy and sensing P-waves without broadcasting atrial event signals.

In the example shown, RV pacemaker 14 is configured to deliver the first ventricular pacing pulse 482 at a shortened AV pacing interval 480 after the detecting atrial event 455 using a physiological atrial event input. RA pacemaker 12 is configured to compare a detected AV pacing interval 476 after withholding a broadcast atrial event signal to a temporary, shortened AV pacing interval 480. By delivering the first pacing pulse 482 at a shortened AV pacing interval 480, RA pacemaker 12 confirms that atrial event detection by RV pacemaker 14 has been restored based on the shortened, detected AV interval 476. In response to detecting the shortened AV interval 476, RA pacemaker 12 terminates the atrial event broadcast mode. On the next cardiac cycle, RV pacemaker 14 continues detecting atrial events from the physiological atrial event input and is configured to resume using the target AV pacing interval 418 corresponding to the selected atrial event input for controlling ventricular pacing pulse delivery.

FIG. 9 is a flow chart 500 of a method performed by RV pacemaker 14 for controlling atrial event input during atrial-synchronized ventricular pacing according to one example. FIG. 10 is a flow chart 600 of a method performed by RA pacemaker 12 operating in cooperation with the RV pacemaker 14 performing the methods of FIG. 9. RA pacemaker 12 is configured to determine appropriate times for broadcasting atrial event signals to support atrial event detection by RV pacemaker 14 when a physiological atrial event input is not reliable for atrial event detection.

At block 502, RV pacemaker control circuit 206 selects an atrial event input used by atrial event detector circuit 240 for detecting atrial events. Control circuit 206 sets the AV pacing interval at block 504 based on the atrial event input selected at block 502. The initial atrial event input may be selected to be A4 events in the motion signal from motion sensor 212. In this case, the AV pacing interval may be set relatively short, e.g., less than 100 ms or 50 ms or less. If the initial atrial event input is selected to be P-wave signals in the cardiac electrical signal, the AV pacing interval may set relatively longer, e.g., greater than 100 ms, such as around 200 to 250 ms. It is recognized that in either case, the AV pacing interval may be an adjustable interval that changes with heart rate determined from detected atrial events.

The initial atrial event input selected at block 502 is typically a physiological atrial event input, such as P-waves or A4 events, which are not arising from a device-generated source. However, in some circumstances, the atrial event input initially selected at block 502 may be broadcast atrial event signals in which case control circuit 206 may set the AV pacing interval to an interval that accounts for differences in relative timing of broadcast atrial events and physiological atrial event signals and/or system delays that may be inherently present between the time of an actual atrial event and the time the RV pacemaker 14 detects the broadcast signal.

At block 506, RV pacemaker 14 operates to deliver atrial-synchronized ventricular pacing using the selected atrial event input and corresponding AV pacing interval. RV pacemaker control circuit 206 controls the pulse generator 202 to deliver ventricular pacing pulses upon expiration of the selected AV pacing interval following atrial events detected from the selected atrial event input.

At block 508, control circuit 206 determines if atrial event detection is lost. Atrial event detection may be determined to be lost when a threshold number of ventricular pacing pulses are delivered at the ventricular LR pacing interval, without atrial event detection during the ventricular cycle. For example, atrial event detection may be determined to be lost when at least three consecutive or non-consecutive ventricular pacing pulses delivered at the ventricular LR pacing interval. The ventricular LR pacing interval may be an adjusted or temporary LR pacing interval to provide rate smoothing to avoid a sudden rate change in some examples.

If atrial event detection is determined to be lost at block 508, control circuit 206 may select a different atrial event input at block 510 for detecting the atrial events, which may be a different physiological atrial event input when available. For example, if the atrial event input selected at block 502 was atrial systolic mechanical events, the atrial event input may be switched to P-wave signals, or vice versa.

Control circuit 206 determines if atrial event detection is restored at block 512 using a different physiological atrial event input. Atrial event detection may be determined to be restored at block 512 in response to a threshold number of atrial event detections, which may be required to be consecutive but may be non-consecutive in some examples, e.g., 6 atrial event detections out of 8 consecutive ventricular cycles. If atrial event detection is restored by using a different physiological atrial event input, the AV pacing interval is adjusted at block 514 according to the atrial event input now being used to maintain the desired synchrony between atrial and ventricular systolic events. The process may return to block 508 such that if atrial event detection is lost again, the atrial event input may be switched back to the first physiological atrial event input or another physiological atrial event input if available, at block 510.

If atrial event detection is not restored from a physiological atrial event input, control circuit 206 switches to a broadcast atrial event input. Control circuit 206 may select the broadcast atrial event input by powering up telemetry circuit 208 for receiving broadcast atrial event communication signals. Additionally or alternatively, control circuit 206 may select the broadcast atrial event input by enabling atrial event detector circuit 240 to detect far-field atrial pacing pulses from the cardiac electrical signal produced by sensing circuit 204 and passed to control circuit 206

At block 518, control circuit 206 may control pulse generator 202 to deliver at least one ventricular pacing pulse at a temporary AV pacing interval in response to detecting the broadcast atrial event. The temporary AV pacing interval may be shorter than the AV pacing interval that is normally selected for use during the selected atrial event input and is used to signal to RA pacemaker 12 that an atrial event has been detected. A temporary AV pacing interval may be used for one or more cardiac cycles each time the atrial event input is switched to enable RA pacemaker 12 to confirm atrial event detection by RV pacemaker 14 is occurring. The AV pacing interval is then adjusted at block 520 to the AV pacing interval that promotes optimal atrioventricular synchrony when a broadcast atrial event input is being used. In other examples, the AV pacing interval may be adjusted at block 520 based on the selected broadcast atrial event input without using a temporary AV pacing interval. RV pacemaker 14 operates to deliver atrial-synchronized ventricular pacing using the selected broadcast atrial event input.

In some cases, the RA pacemaker 12 may broadcast a high energy atrial pacing pulse and/or a refractory pacing pulse on paced atrial cycles and broadcast a wireless communication signal via telemetry circuit 308 when an intrinsic atrial P-wave is sensed. In other cases, RA pacemaker 12 may transmit two different, coded wireless communication signals by telemetry circuit 308, one indicating when an atrial paced event occurs and a different one when an atrial sensed event occurs. In still other examples, RA pacemaker 12 may deliver a double pacing pulse (one to capture the RA and one delivered within the absolute refractory period of the RA) to indicate a paced atrial event and deliver a signal pacing pulse during the absolute atrial refractory period following a sensed P-wave to indicate a sensed atrial event. RV pacemaker control circuit 206 may set the AV pacing interval at block 520 to either a paced AV pacing interval or a sensed AV pacing interval according to the detected broadcast atrial event.

Control circuit 206 may determine when a predetermined number of broadcast atrial events have been detected at block 522, and switch back to a physiological atrial event input at block 524. Control circuit 206 determines if atrial event detection using the physiological atrial event input is restored at block 512. If more than one physiological atrial event input is available, each available physiological input may be tested at block 512 until a physiological input is identified that results in reliable atrial event detection. If atrial event detection from a physiological atrial event input is not restored, atrial event detector circuit 240 may continue detecting atrial events from broadcast atrial event input (block 516). If atrial event detection from the physiological atrial event input is restored, RV pacemaker 14 adjusts the AV pacing interval according to the selected atrial event input and returns to block 506 for delivering atrial-synchronized ventricular pacing using the selected atrial event input.

The operations of RA pacemaker 12 performed during the operations of RV pacemaker 14 described in conjunction with FIG. 9 are shown by the flow chart of FIG. 10. At block 602, RA pacemaker control circuit 306 detects a far-field ventricular event, e.g., a far-field R-wave or a ventricular pacing pulse, from the cardiac electrical signal received by sensing circuit 304. Control circuit 306 determines the detected AV interval at block 604 between the far-field electrical event and a most recent atrial paced or sensed event.

The detected AV interval is compared to the expected AV pacing interval at block 606. RA pacemaker 12 may be programmed to store the AV pacing intervals used by RV pacemaker 14 for each corresponding atrial event input. RA pacemaker 12 may retrieve the AV pacing intervals programmed for use for each of the available physiological atrial event inputs and compare the detected AV interval to each of the possible AV pacing intervals that RV pacemaker 14 is expected to be using if RV pacemaker 14 detected the most recent atrial event from a physiological atrial event input. The detected AV interval may be compared to one or more possible AV pacing interval ranges corresponding to each physiological atrial event input available in RV pacemaker 14.

If the detected AV interval matches a stored AV pacing interval expected to be used by RV pacemaker during physiological atrial event input (at block 606), e.g., within a predefined matching range, RA pacemaker 12 continues to detect far-field ventricular events by returning to block 602 and monitoring the detected AV intervals. The detected AV interval may be determined to match an expected AV pacing interval when the detected AV interval is within a predetermined range, e.g., within 10 ms, within 20 ms or within 50 ms or less, than an expected AV pacing interval. If the detected AV interval does not match an expected AV pacing interval, the RA pacemaker 12 begins to broadcast atrial event signals at block 608.

The atrial event signals may be broadcast as described above. For example, broadcast atrial event signals may include coded wireless communication signals indicating either a paced or sensed atrial event, atrial pacing pulses and/or atrial refractory pacing pulses, both of which may be delivered using increased pacing pulse energy greater than the pacing pulse energy used to pace the atria when RA pacemaker 12 is not broadcasting atrial event signals.

Upon broadcasting the first atrial event signal, RA pacemaker control circuit 306 determines the AV interval as the time from the broadcast atrial event signal (or corresponding atrial event) to the next detected far-field ventricular event at block 610 and compares the detected AV interval to an expected AV interval. The expected AV interval may be a programmed AV pacing interval that RV pacemaker 14 is expected to use when the broadcast atrial event signal is detected. The expected AV interval may be a temporary, shortened AV pacing interval as described in conjunction with block 518 of FIG. 9.

If the detected AV interval matches an expected AV interval, as determined at block 610, e.g., within a matching range of +10 to 20 ms, the process advances to block 614. If not, RA pacemaker 12 may adjust the broadcast atrial event signal at block 612 to increase the likelihood of being detected by RV pacemaker 14. RA pacemaker 12 may adjust the broadcast atrial event signal by changing the type of signal (e.g., from a transmitted communication signal to an atrial pacing pulse or vice versa) or increasing the amplitude or strength of the broadcast atrial signal.

Once detection of the broadcast atrial event signal by RV pacemaker 14 is confirmed, based on the detected AV interval matching the expected AV interval at block 610, RA pacemaker 12 broadcasts a predetermined number of atrial event signals. After the predetermined number of atrial event signals are broadcast, RA pacemaker 12 may withhold one or more broadcast atrial event signals at block 614. RA pacemaker control circuit 306 determines the detected AV interval on the one or more cardiac cycles that the broadcast atrial event signal is withheld and compares the detected AV interval to the expected AV pacing interval at block 616. If the detected AV interval matches the expected AV pacing interval, RA pacemaker 12 may terminate broadcasting atrial event signals at block 618 and return to block 602 for monitoring detected AV intervals for detecting a loss of atrial event detection by RV pacemaker 14. If the detected AV interval does not match the expected AV interval, RA pacemaker resumes broadcasting atrial event signals at block 608.

In other examples, rather than withholding the broadcast atrial event signal(s) at block 614, RA pacemaker 12 may monitor the detected AV intervals at block 616 for detecting a temporary, shortened AV interval while still broadcasting atrial event signals. RV pacemaker 14 may be configured to continue detecting the broadcast atrial event signals, but periodically check if atrial event detection from a physiological atrial event input is restored (blocks 514 and 512 of FIG. 9). Atrial event detector circuit 240 may be configured to detect atrial events from both a physiological atrial event input and the broadcast atrial event input for one or more cycles to maintain proper AV synchrony while checking if atrial event detection from a physiological atrial event input is restored. If restored, RV pacemaker 14 may signal RA pacemaker 12 that AV event signal broadcasting is no longer required by delivering one or more ventricular pacing pulses at a "coded" temporary, shortened AV pacing interval. The RA pacemaker detects the "coded" shortened AV pacing interval and terminates atrial event broadcasting at block 618. RV pacemaker 14 switches the atrial event input to the physiological input and adjusts the AV pacing interval as needed at block 514 (FIG. 9).

Thus, various methods for controlling atrial event input and detection in an intracardiac pacemaker system configured to deliver ventricular pacing in an atrial-synchronized pacing mode have been described according to illustrative embodiments. In other examples, various methods described herein may include steps performed in a different order or combination than the illustrative examples shown and described herein. Furthermore, other circuitry may be conceived by one of ordinary skill in the art for implementing the techniques disclosed herein; the particular examples described herein are illustrative in nature and not intended to be limiting. It is appreciated that various modifications to the referenced examples may be made without departing from the scope of the disclosure and the following claims.

The invention claimed is:
1. A medical device, comprising:
 a sensing circuit configured to:
  sense a first physiological cardiac signal;
  sense first atrial event signals from the first physiological cardiac signal;
  sense a second physiological cardiac signal; and
  sense second atrial event signals from the second physiological cardiac signal; and
 a control circuit coupled to the sensing circuit and configured to:
  receive an atrial event input from the sensing circuit based on a first selected one of the first atrial event signals sensed by the sensing circuit or the second atrial event signals sensed by the sensing circuit;
  determine that atrial event input switching criteria are met; and switch to receiving the atrial event input based on a second selected one of the first atrial event signals sensed by the sensing circuit or the second atrial event signals sensed by the sensing circuit in response to the atrial event input switching criteria being met.

2. The medical device of claim 1, further comprising a pulse generator configured to generate pacing pulses wherein:
the control circuit is configured to:
start an atrioventricular pacing interval in response to receiving the atrial event input; and
determine that the atrioventricular pacing interval expires; and
the pulse generator is configured to generate a ventricular pacing pulse in response to the atrioventricular pacing interval expiring.

3. The medical device of claim 1, wherein the sensing circuit comprises a cardiac electrical signal sensing circuit configured to:
sense the first physiological cardiac signal by sensing a cardiac electrical signal; and
sense the first sensed atrial event signals by sensing atrial P-waves from the cardiac electrical signal.

4. The medical device of claim 1, wherein the sensing circuit comprises a motion sensor configured to produce the second physiological cardiac signal as a motion signal and sense the second atrial event signals from the motion signal.

5. The medical device of claim 1, wherein the control circuit is configured to:
determine a change in heart rate based on at least one of the first physiological cardiac signal and the second physiological cardiac signal; and
determine that the input switching criteria are met based at least on the determined change in heart rate.

6. The medical device of claim 1, wherein:
the sensing circuit comprises a motion sensor configured to sense a motion signal; and
the control circuit is configured to:
determine a change in patient posture from the motion signal; and
determine that the input switching criteria are met based at least on the determined change in patient posture.

7. The medical device of claim 1, wherein:
the sensing circuit comprises a motion sensor configured to produce a motion signal; and
the control circuit is configured to:
determine a change in patient physical activity from the motion signal; and
determine that the input switching criteria are met based at least on the determined change in patient physical activity.

8. The medical device of claim 1, further comprising a pulse generator configured to generate pacing pulses and wherein:
the control circuit is configured to:
start a ventricular lower rate pacing interval;
determine that the ventricular lower rate pacing interval expires without receiving the atrial event input from the sensing circuit;
the pulse generator is configured to generate a pacing pulse in response to the ventricular lower rate pacing interval expiring; and
the control circuit is further configured to:
determine that a threshold number of pacing pulses are generated by the pulse generator at the ventricular lower rate pacing interval due to the ventricular lower rate pacing interval expiring without receiving the atrial event input; and
determine that the input switching criteria are met by at least determining that the threshold number of pacing pulses are generated by the pulse generator at the ventricular lower rate pacing interval.

9. The medical device of claim 1, wherein the control circuit is configured to:
determine that less than a threshold number of the first selected one of first atrial event signals sensed from the first physiological cardiac signal or the second atrial event signals sensed from the second physiological cardiac signal are sensed by the sensing circuit during a predetermined number of ventricular cycles; and
determine that the atrial event input switching criteria are met in response to less than the threshold number of the first selected one of first atrial event signals sensed from the first physiological cardiac signal or the second atrial event signals sensed from the second physiological cardiac signal being sensed by the sensing circuit during the predetermined number of ventricular cycles.

10. The medical device of claim 1, further comprising:
a housing enclosing the control circuit and the sensing circuit;
a plurality of electrodes carried by the housing; and
a motion sensor enclosed by the housing;
wherein the sensing circuit is configured to sense the first physiological cardiac signal via the plurality of electrodes carried by the housing and the second physiological cardiac signal via the motion sensor.

11. A method, comprising:
receiving by a processor an atrial event input based on a first selected one of first atrial event signals sensed from a first physiological cardiac signal or second atrial event signals sensed from a second physiological cardiac signal;
determine that atrial event input switching criteria are met; and
switching to receiving the atrial event input based on a second selected one of the first atrial event signals sensed from the first physiological cardiac signal or the second atrial event signals sensed from the second physiological cardiac signal in response to the atrial event input switching criteria being met.

12. The method of claim 11, further comprising:
starting an atrioventricular pacing interval in response to receiving the atrial event input;
determining that the atrioventricular pacing interval expires; and
generating a ventricular pacing pulse in response to the atrioventricular pacing interval expiring.

13. The method of claim 11, further comprising:
sensing the first physiological cardiac signal by sensing a cardiac electrical signal; and
sensing the first sensed atrial event signals by sensing atrial P-waves from the cardiac electrical signal.

14. The method of claim 11, further comprising sensing the second physiological cardiac signal by producing a motion signal by a motion sensor and sensing the second atrial event signals from the motion signal.

15. The method of claim 11, further comprising:
determining a change in heart rate based on at least one of the first physiological cardiac signal and the second physiological cardiac signal; and
determining that the input switching criteria are met based at least on the determined change in heart rate.

16. The method of claim 11, further comprising:
producing a motion signal by a motion sensor;
determining a change in patient posture from the motion signal; and
determining that the input switching criteria are met based at least on the determined change in patient posture.

17. The method of claim 11, further comprising:
producing a motion signal by a motion sensor;
determining a change in patient physical activity from the motion signal; and
determining that the input switching criteria are met based at least on the determined change in patient physical activity.

18. The method of claim 11, further comprising:
starting a ventricular lower rate pacing interval;
determining that the ventricular lower rate pacing interval expires without receiving the atrial event input;
generating a pacing pulse in response to the ventricular lower rate pacing interval expiring;
determining that a threshold number of pacing pulses are generated at the ventricular lower rate pacing interval due to the ventricular lower rate pacing interval expiring without receiving the atrial event input; and
determining that the input switching criteria are met by at least determining that the threshold number of pacing pulses are generated at the ventricular lower rate pacing interval.

19. The method of claim 11, further comprising:
determining that less than a threshold number of the first selected one of the first atrial event signals sensed from the first physiological cardiac signal or the second atrial event signals sensed from the second physiological cardiac signal are sensed during a predetermined number of ventricular cycles; and
determining that the atrial event input switching criteria are met in response to less than the threshold number of the first selected one of first atrial event signals sensed from the first physiological cardiac signal or the second atrial event signals sensed from the second physiological cardiac signal being sensed during the predetermined number of ventricular cycles.

20. A non-transitory, computer-readable medium storing a set of instructions, which, when executed by control circuitry of a medical device, cause the medical device to:
sense a first physiological cardiac signal;
sense first atrial event signals from the first physiological cardiac signal;
sense a second physiological cardiac signal;
sense second atrial event signals from the second physiological cardiac signal;
receive by a processor of the medical device an atrial event input based on a first selected one of the first atrial event signals and the second atrial event signals;
determine that atrial event input switching criteria are met; and
switch to receiving the atrial event input based on a second selected one of the first atrial event signals or the second atrial event signals in response to the atrial event input switching criteria being met.

21. The medical device of claim 1 wherein the sensing circuit is further configured to sense the second atrial event signals by sensing mechanical event signals arising from atrial contraction from the second physiological cardiac signal.

* * * * *